United States Patent
Sarphati et al.

(10) Patent No.: US 12,194,166 B2
(45) Date of Patent: Jan. 14, 2025

(54) STERILIZATION TRAY

(71) Applicant: Zuno Medical, Inc., San Jose, CA (US)

(72) Inventors: Joffrey Sarphati, San Jose, CA (US); Christopher Feezor, San Jose, CA (US); Michael Olmes, San Jose, CA (US)

(73) Assignee: ZUNO MEDICAL, INC., Campbell, CA (US)

( * ) Notice: Subject to any disclaimer, the term of this patent is extended or adjusted under 35 U.S.C. 154(b) by 0 days.

(21) Appl. No.: 18/488,824

(22) Filed: Oct. 17, 2023

(65) Prior Publication Data

US 2024/0058485 A1 Feb. 22, 2024

Related U.S. Application Data

(63) Continuation of application No. 17/222,800, filed on Apr. 5, 2021, now Pat. No. 11,826,479, which is a
(Continued)

(51) Int. Cl.
*A61L 2/07* (2006.01)
*A61L 2/26* (2006.01)

(52) U.S. Cl.
CPC ..................... *A61L 2/07* (2013.01); *A61L 2/26* (2013.01); *A61L 2202/122* (2013.01); *A61L 2202/24* (2013.01)

(58) Field of Classification Search
CPC .......... A61L 2/07; A61L 2/26; A61L 2202/24; A61L 2202/122
See application file for complete search history.

(56) References Cited

U.S. PATENT DOCUMENTS

| 4,022,324 A | 5/1977 | Schuster |
| 4,105,407 A | 8/1978 | Sanderson |

(Continued)

FOREIGN PATENT DOCUMENTS

| CN | 202761746 U | 3/2013 |
| JP | 2001192014 A | 7/2001 |

(Continued)

OTHER PUBLICATIONS

U.S. Appl. No. 14/909,387, Non-Final Office Action, Mailed on Jul. 20, 2017, 9 pages.
(Continued)

*Primary Examiner* — Sean E Conley
*Assistant Examiner* — Brendan A Hensel
(74) *Attorney, Agent, or Firm* — Kilpatrick Townsend & Stockton LLP

(57) ABSTRACT

An apparatus for sterilizing items and storing the sterilized items prior to use includes a container configured to receive items to be sterilized, a trap door coupled with the container, and a mechanism operatively coupled with the trap door and the container. The trap door is reconfigurable between an open configuration providing a fluid passage into the apparatus and a closed configuration in which the items are sealed within the apparatus. The mechanism is configured for selective reconfiguration of the trap door from the closed configuration to the open configuration and to automatically reconfigure the trap door from the open configuration to the closed configuration after completion of a sterilization cycle for items disposed within the apparatus.

20 Claims, 18 Drawing Sheets

Related U.S. Application Data continuation of application No. 15/750,472, filed as application No. PCT/US2016/045869 on Aug. 5, 2016, now Pat. No. 10,967,079.

(60) Provisional application No. 62/202,105, filed on Aug. 6, 2015.

(56) References Cited

U.S. PATENT DOCUMENTS

| | | | |
|---|---|---|---|
| 4,124,141 A | 11/1978 | Armentrout et al. | |
| 4,149,650 A | 4/1979 | Whelchel et al. | |
| 4,196,166 A | 4/1980 | Sanderson et al. | |
| 4,228,914 A | 10/1980 | Sanderson | |
| 4,247,517 A | 1/1981 | Sanderson et al. | |
| 4,251,482 A | 2/1981 | Sanderson et al. | |
| D264,503 S | 5/1982 | Sanderson et al. | |
| 4,349,118 A | 9/1982 | Sanderson et al. | |
| 4,372,921 A | 2/1983 | Sanderson et al. | |
| 4,374,570 A | 2/1983 | Sanderson et al. | |
| D268,867 S | 5/1983 | Sanderson et al. | |
| 4,416,417 A | 11/1983 | Sanderson et al. | |
| 4,457,327 A | 7/1984 | Pepper | |
| D275,229 S | 8/1984 | Sanderson et al. | |
| 4,466,552 A | 8/1984 | Butterworth et al. | |
| 4,482,053 A | 11/1984 | Alpern et al. | |
| 4,558,632 A | 12/1985 | Sanderson et al. | |
| 4,583,643 A | 4/1986 | Sanderson | |
| 4,584,182 A | 4/1986 | Sanderson et al. | |
| 4,612,872 A | 9/1986 | Whelchel et al. | |
| 4,716,025 A | 12/1987 | Nichols | |
| 4,748,003 A | 5/1988 | Riley | |
| 4,754,595 A | 7/1988 | Sanderson | |
| 4,774,063 A | 9/1988 | Runnells | |
| 4,915,913 A | 4/1990 | Williams et al. | |
| 4,948,566 A * | 8/1990 | Gabele | A61L 2/06 422/310 |
| 5,223,229 A | 6/1993 | Brucker | |
| 5,277,876 A | 1/1994 | Wagner | |
| 5,308,058 A | 5/1994 | Mandel et al. | |
| 5,352,416 A | 10/1994 | Wagner | |
| 5,368,821 A | 11/1994 | Schmoegner et al. | |
| 5,590,778 A | 1/1997 | Dutchik | |
| 6,837,027 B2 | 1/2005 | Hickey | |
| 7,132,089 B2 | 11/2006 | Lacabanne | |
| 7,198,760 B1 | 4/2007 | Wagner | |
| 7,942,264 B2 | 5/2011 | Friderich et al. | |
| 8,006,982 B2 | 8/2011 | Whitlow et al. | |
| 8,327,606 B2 | 12/2012 | Kemp et al. | |
| 9,057,657 B2 | 6/2015 | Heckenberger et al. | |
| 10,022,464 B2 | 7/2018 | Sarphati et al. | |
| 10,967,079 B2 | 4/2021 | Sarphati et al. | |
| 2008/0236631 A1* | 10/2008 | Lin | A61L 2/07 134/95.1 |
| 2012/0082589 A1 | 4/2012 | Ladison et al. | |
| 2012/0156096 A1 | 6/2012 | Allen et al. | |
| 2012/0189508 A1 | 7/2012 | Kreidler | |
| 2013/0280134 A1 | 10/2013 | Hoffman et al. | |
| 2014/0056759 A1 | 2/2014 | Jacene et al. | |
| 2015/0374868 A1 | 12/2015 | Bruce et al. | |
| 2016/0193374 A1 | 7/2016 | Sarphati et al. | |

FOREIGN PATENT DOCUMENTS

| | | |
|---|---|---|
| JP | 2008184203 A | 8/2008 |
| WO | 2014159696 A1 | 10/2014 |
| WO | 2015017828 | 2/2015 |
| WO | 2017024260 | 2/2017 |

OTHER PUBLICATIONS

U.S. Appl. No. 14/909,387, Notice of Allowance, Mailed on Mar. 16, 2018, 5 pages.
U.S. Appl. No. 15/750,472, Advisory Action, Mailed on May 21, 2020, 3 pages.
U.S. Appl. No. 15/750,472, Final Office Action, Mailed on Dec. 9, 2019, 17 pages.
U.S. Appl. No. 15/750,472, Non-Final Office Action, Mailed on May 14, 2019, 21 pages.
U.S. Appl. No. 15/750,472, Notice of Allowance, Mailed on Dec. 2, 2020, 7 pages.
U.S. Appl. No. 17/222,800, Non-Final Office Action, Mailed on Dec. 21, 2022, 8 pages.
U.S. Appl. No. 17/222,800, Notice of Allowance, Mailed on Jul. 18, 2023, 7 pages.
Application No. PCT/US2014/049480, International Preliminary Report on Patentability, Mailed on Feb. 11, 2016, 8 pages.
Application No. PCT/US2014/049480, International Search Report and Written Opinion, Mailed on Nov. 5, 2014, 10 pages.
Application No. PCT/US2016/045869, International Preliminary Report on Patentability, Mailed on Feb. 15, 2018, 9 pages.
Application No. PCT/US2016/045869, International Search Report and Written Opinion, Mailed on Oct. 6, 2016, 10 pages.

* cited by examiner

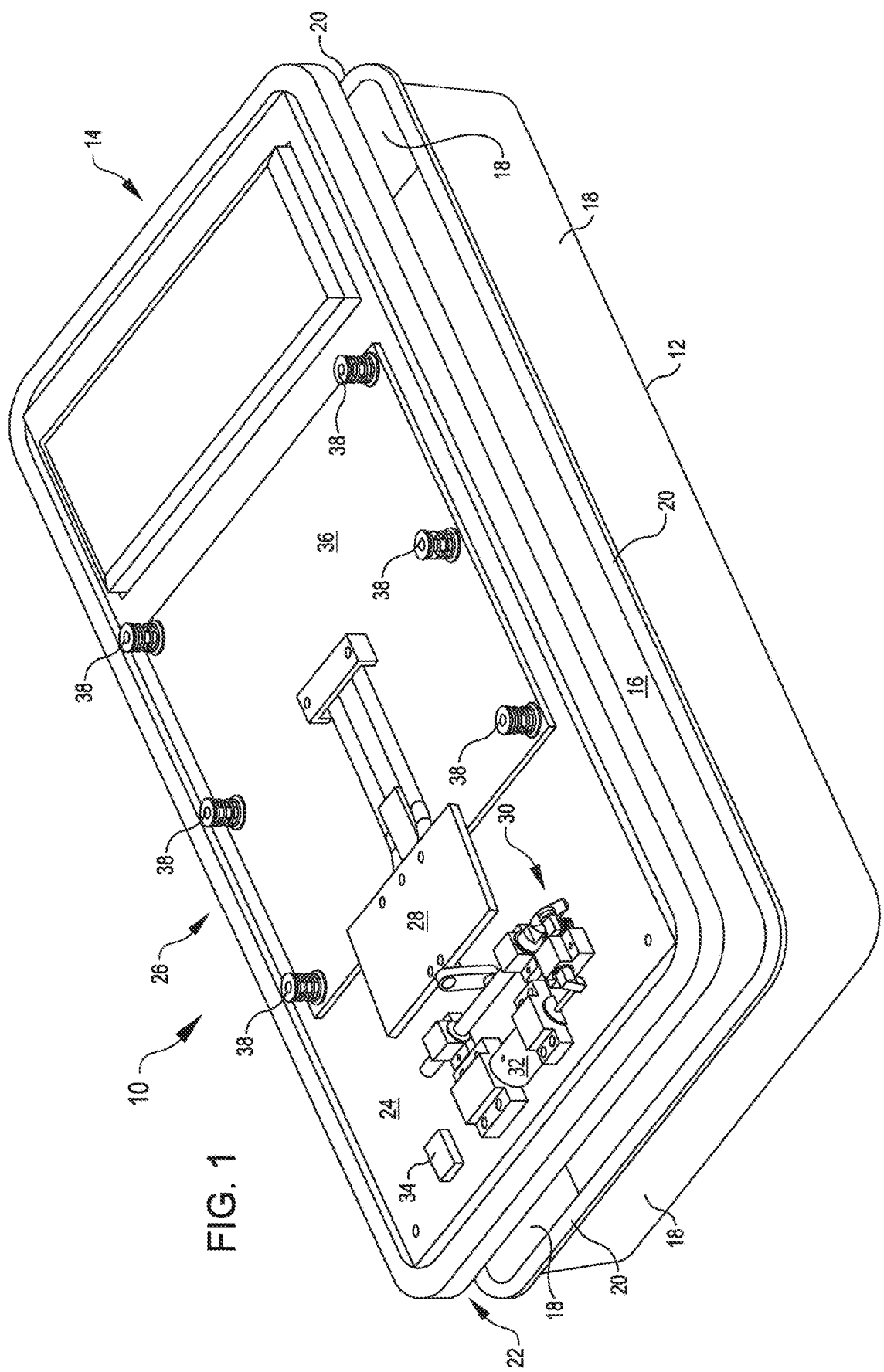

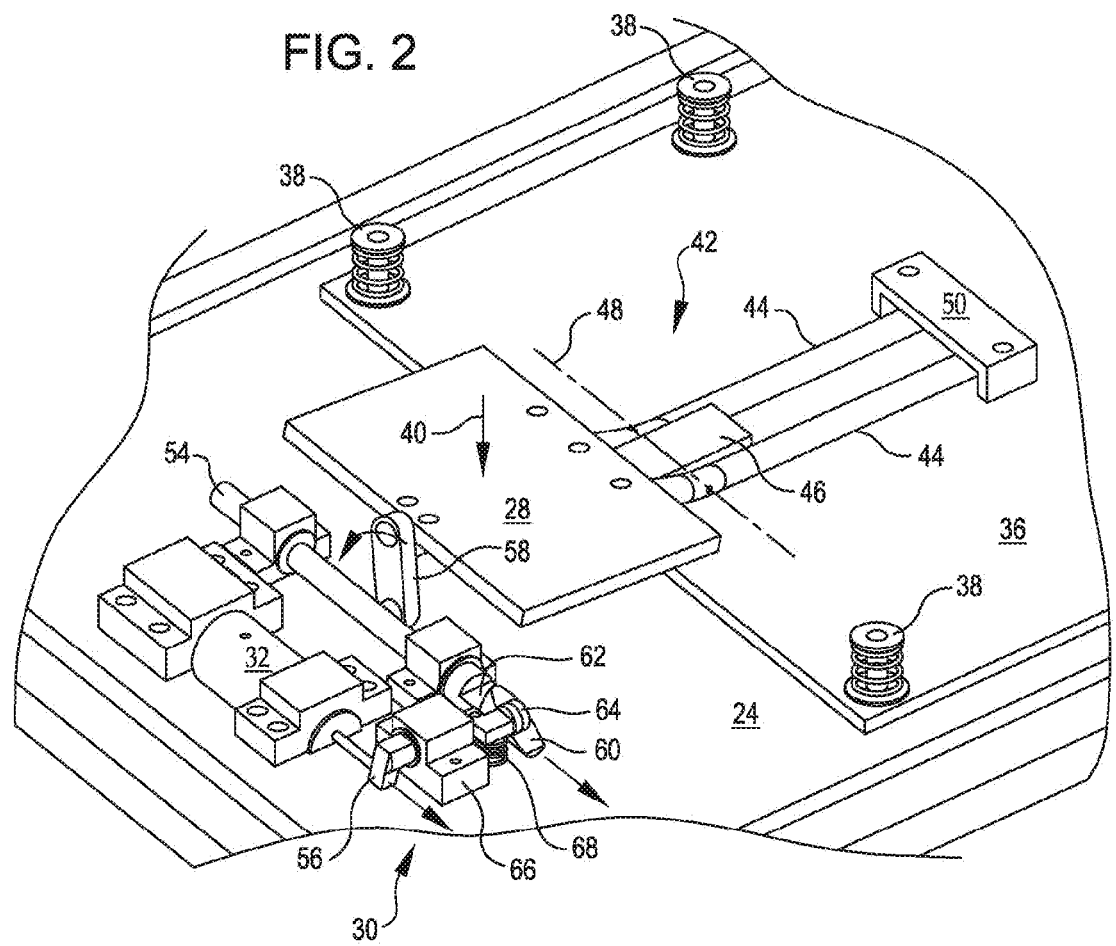

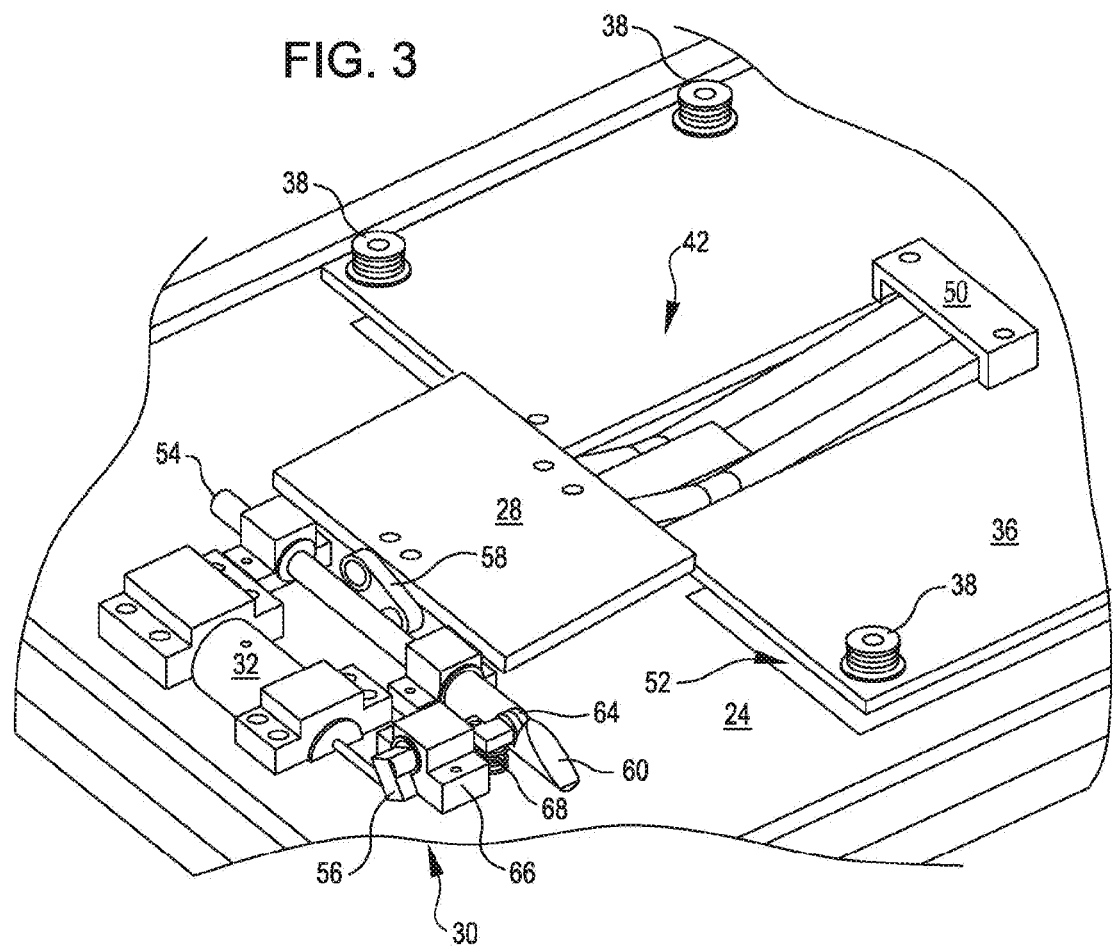

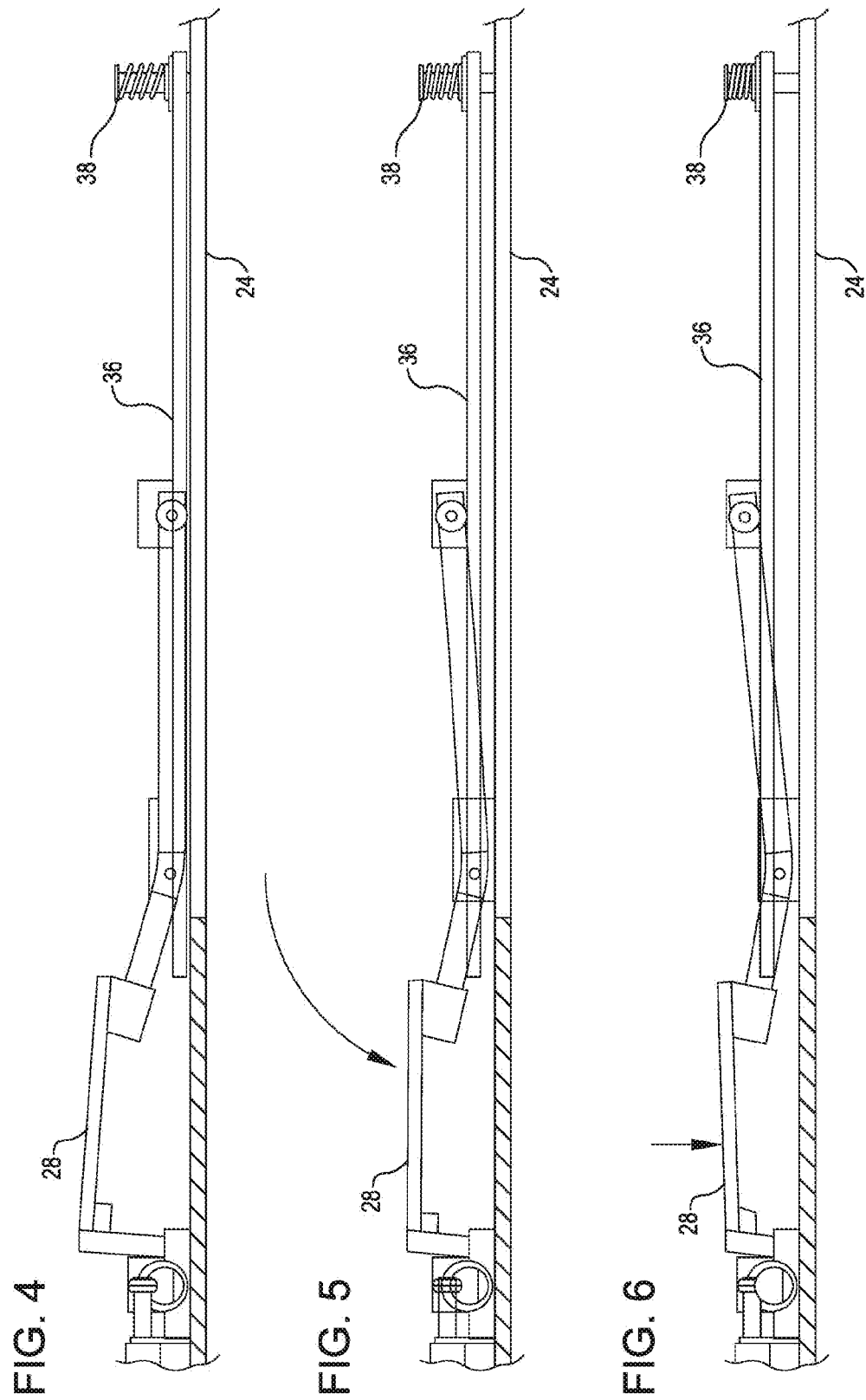

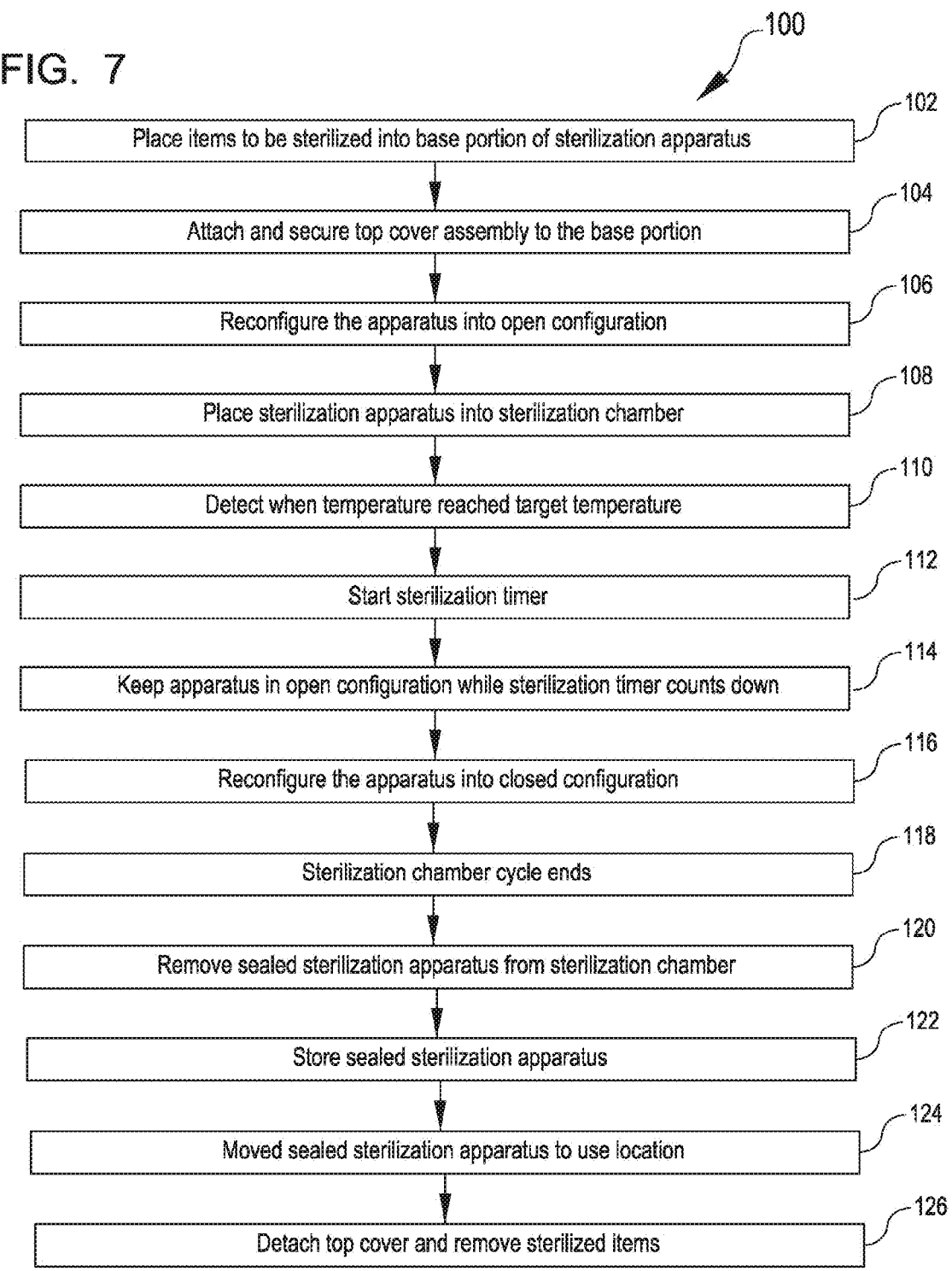

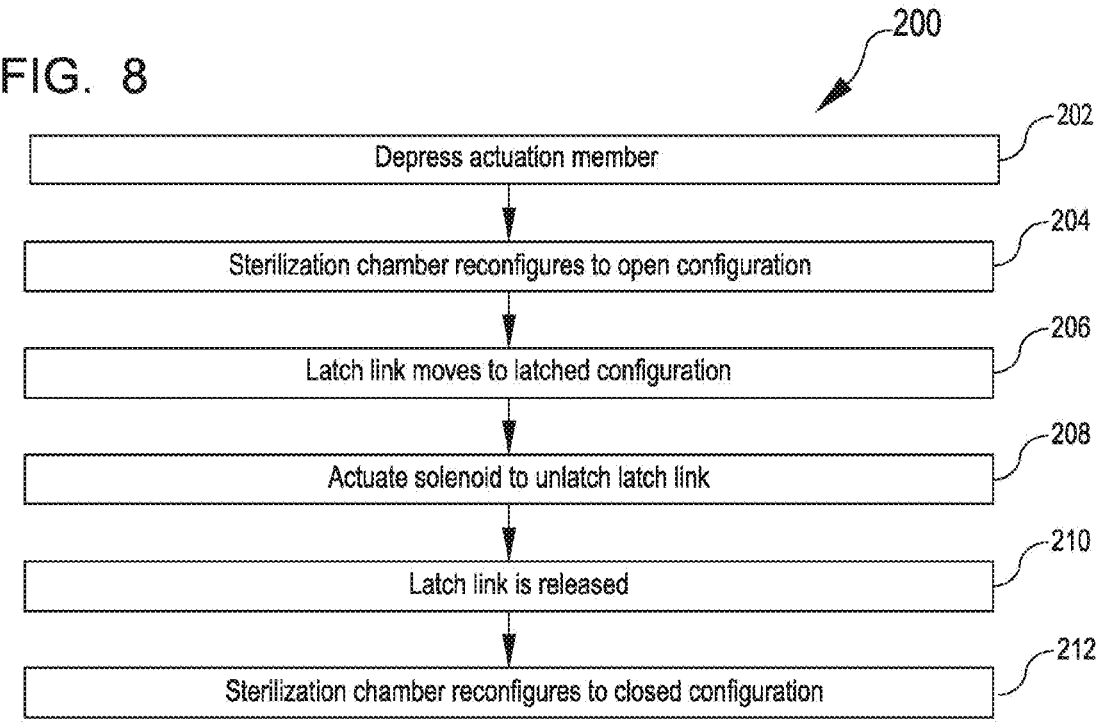
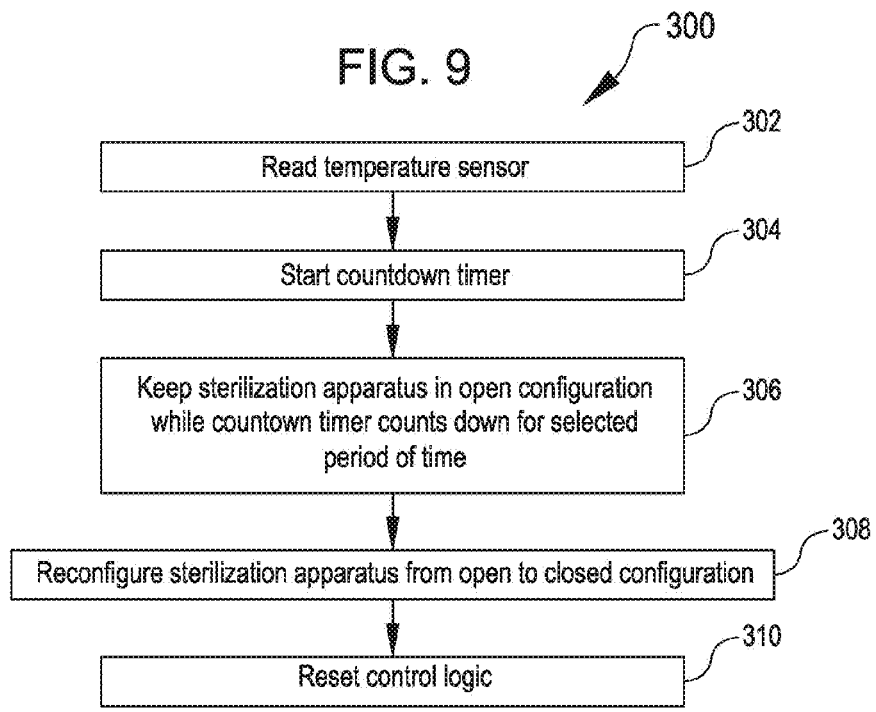

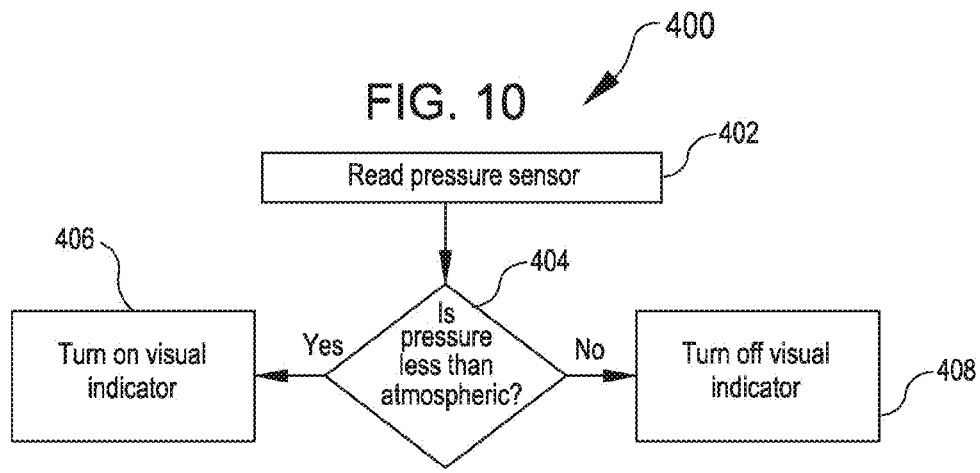
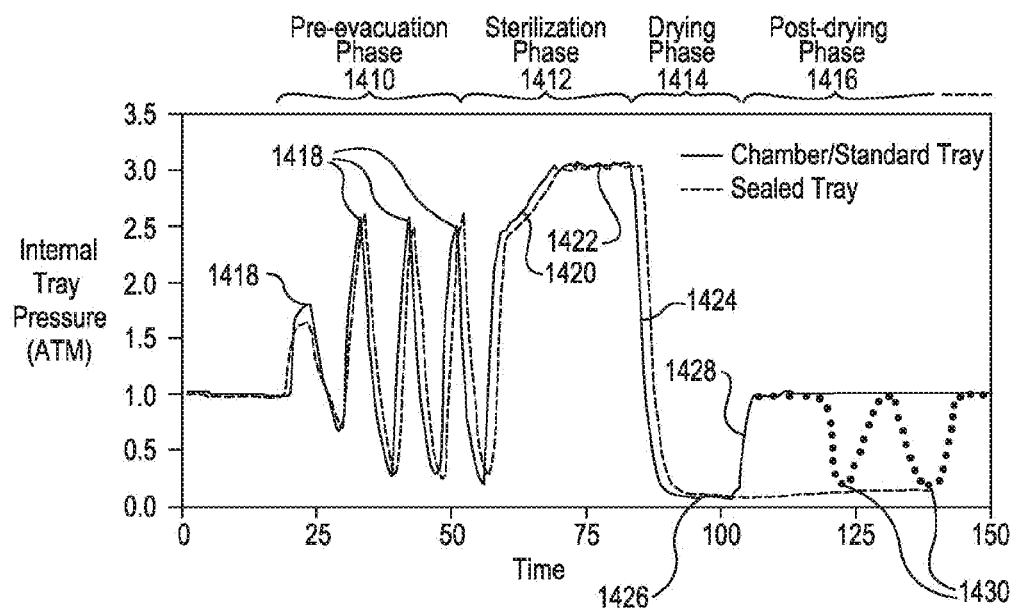

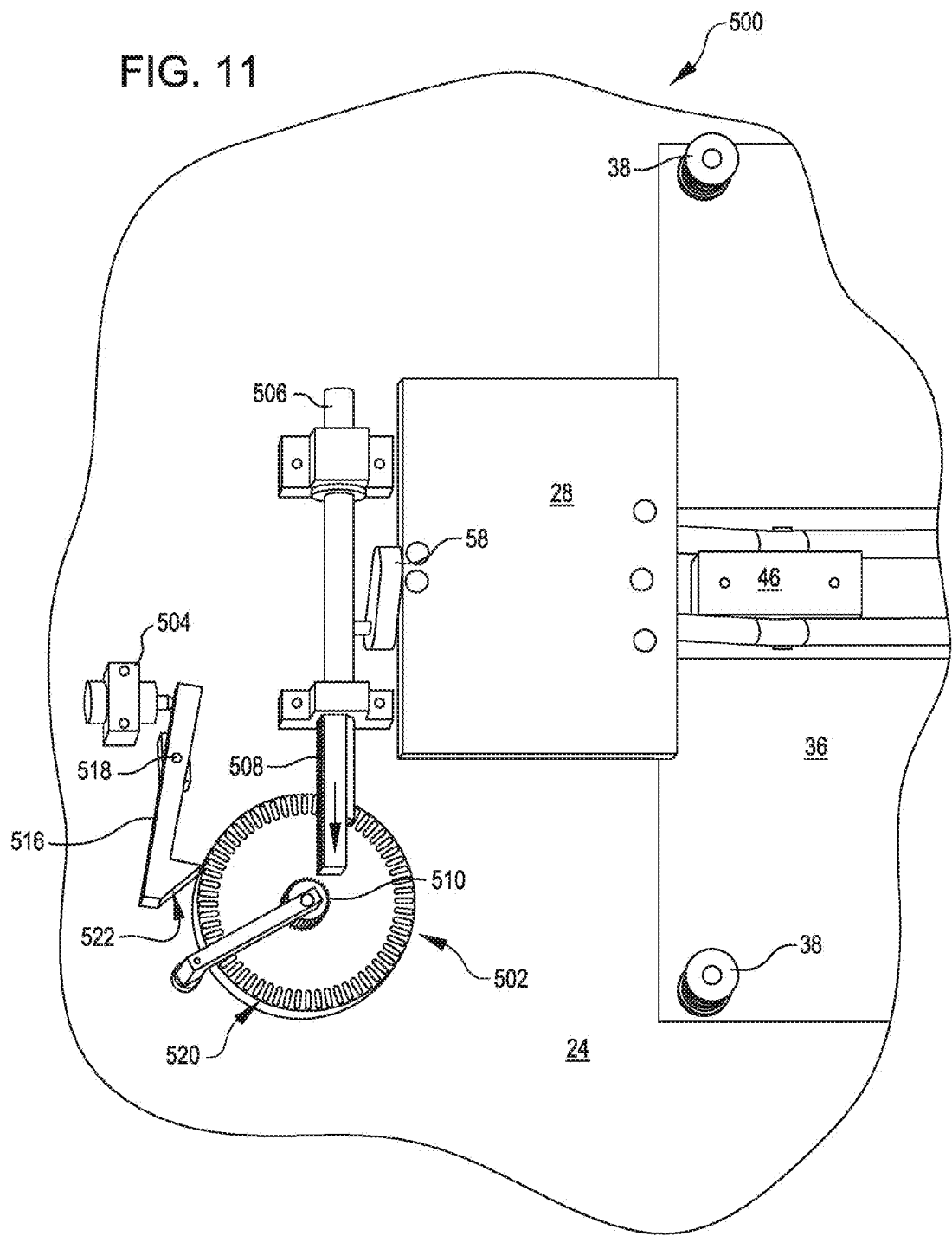

STERILIZATION TRAY

CROSS-REFERENCE TO RELATED APPLICATIONS

This application is a continuation of U.S. application Ser. No. 17/222,800, filed Apr. 5, 2021, which is a continuation of U.S. application Ser. No. 15/750,472, filed Feb. 5, 2018, which is a U.S. 371 of International Application No. PCT/US2016/045869, filed Aug. 5, 2016, which claims the benefit of U.S. Provisional Application No. 62/202,105, filed Aug. 6, 2015, titled "STERILIZATION TRAY," the entire contents of which are hereby incorporated in their entirety for all purposes.

BACKGROUND

Sterilization of items is used in various industries, including health care, pharmaceutical, and food processing industries. A common and proven method used for sterilization applies pressurized high temperature steam in a pressure chamber or vessel for a prescribed period of time. Pressurized high temperature steam within a stainless steel pressure chamber is used for sterilization of laboratory equipment and in the industrial manufacturing sector.

In hospital and health care environments, laboratory environments, and in the pharmaceutical and food processing industry, sterilization may be accomplished by contacting the item to be sterilized with high temperature steam within a pressure vessel. Alternatively, the item to be sterilized can be contacted with a low temperature sterilizing medium (e.g., ethylene oxide or equivalent low temperature sterilizing medium) in a pressure vessel. Various types of sterilization pressure vessels and autoclave chambers can be used utilized to sterilize items. In many instances, the sterilizing medium is contacted with the item being sterilized.

At the end of a sterilization cycle, items inside the sterilization chamber are sterile. Unfortunately, the air in the room where the sterilization chamber is installed will typically contain dust particles, which may carry micro-organisms. Accordingly, sterilized items taken out of a sterilization chamber may become contaminated. Additionally, sterilized items may be stored for a period of time before use. Moreover, in a hospital setting, sterilized items will typically be transported through the hospital to where they are used. Accordingly, sterilized items, when not protected, may be re-contaminated prior to use.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Apparatus and related methods are provided for sterilizing items (e.g., surgical instruments, instrument trays, implants, and/or implant trays) within a sterilization chamber and subsequent storage and/or transportation thereof until use. An example apparatus includes a container having an internal volume into which items to be sterilized are placed. The apparatus is configurable into an open configuration in which the internal volume is in fluid communication with the surrounding environment. The apparatus (and the items to be sterilized therein) is placed into a sterilization chamber (e.g., an autoclave). The apparatus is configured to reconfigure into a closed configuration in which the internal volume is hermetically isolated from the surrounding environment. The reconfiguration to the closed configuration occurs automatically in response to the presence of a vacuum and/or other certain desirable environmental conditions within the sterilization chamber, such as may occur after the completion of a sterilization phase. The sterilization phase can be any suitable portion of a cycle, for example, where the temperature inside the apparatus is greater than a selected sterilization temperature for at least a predetermined amount of time. The apparatus can remain in the closed configuration with its contents hermetically sealed within the apparatus until when the sterilized items are used, thereby preventing recontamination of the sterilized items prior to use. The apparatus can be reused for sterilizing additional batches of items, thereby providing an effective and economical means to sterilize items and to store and/or transport the sterilized items within a healthcare facility or between healthcare facilities prior to use.

The apparatus disclosed herein can be used for the sterile processing of instrumentation, implants, or other items for a hospital or other healthcare facility. The apparatus may be used for sterile processing at the healthcare facility or at a remote site and transported to a healthcare facility while maintaining the sterile state of the items within the apparatus.

In the operation of certain embodiments of the apparatus disclosed herein, instrument trays and/or other items to be sterilized are placed into a base portion of the apparatus, and a sterilization lid is attached to the base portion. A user arranges the lid or features or mechanisms associated with the lid in an open configuration such that the volume inside the tray is in fluid communication with the surrounding environment. For example, the user can orient a trap door on the lid so that the trap door permits fluid communication through the lid. As examples, a user may press down on an actuation member on the sterilization lid to open the trap door, a user may lift up on the trap door to lock it in the open configuration, the user may cause power to be provided to an electro-mechanical actuator which opens the trap door by generating an electro-magnetic force, etc. The trap door may be held open by any suitable latch mechanism or force, including, but not limited to, a mechanical, electro-magnetic, or magnetic features.

When the contents of the apparatus are ready to be sterilized, the apparatus is positioned within a sterilization chamber (e.g., an autoclave) with the lid of the apparatus in the open configuration, and a sterilization cycle is initiated. At the beginning or at a particular point after the start of the sterilization cycle, the apparatus becomes sensitive to—and/or begins monitoring—one or more environmental conditions within the chamber. For example, the apparatus can employ any suitable mechanical or electronic sensor, transducer, etc. for measuring any pertinent environmental condition including, but not limited to, pressure, temperature, and/or humidity. The apparatus can additionally or alternatively include a mechanical or electronic timer to measure any pertinent time segment, including, but not limited to, time elapsed since reaching a particular threshold and/or duration of conditions within relevant ranges. In some aspects, the apparatus is sensitive to conditions by generating power as a result of condition changes or fluctuations. Furthermore, the apparatus may respond to a particular condition or time based on the status of some other time threshold and/or environmental condition threshold. As examples, the apparatus may begin monitoring temperature after a certain amount of time has elapsed since initiating the sterilization cycle, and/or may track a pressure level or duration of time only as long as a temperature is above a certain threshold or within a certain range.

Once environmental conditions within the sterilization chamber satisfy certain criteria (e.g., pressure reaching a particular sub-atmospheric level after a sufficient duration of exposure to high temperatures has elapsed to confirm adequate sterilization of items), the apparatus is reconfigured from the open configuration to the closed configuration, thereby sealing the apparatus, e.g., by releasing the trap door and/or moving it from the open configuration to the closed configuration. Sealing the apparatus (e.g., closing the trap door) hermetically isolates the sterilized items from the outside world and maintains environmental conditions (e.g., pressure and humidity) that existed within the sterilization chamber and equally within the apparatus at the time of reconfiguration, despite additional changes that may occur within the sterilization chamber and/or the external environment. The apparatus can remain sealed until the sterilized items are accessed for use in an operating room.

Thus, in various aspects, an apparatus is provided for sterilizing surgical implements within a sterilization chamber and storing the sterilized surgical implements prior to use. The apparatus includes a container configured to receive one or more surgical implements, a trap door coupled with the container, and a mechanism operatively coupled with the trap door and the container. The trap door is coupled with the container so as to be reconfigurable between a closed configuration and an open configuration. In the closed configuration, the trap door and the container at least partially define an internal volume that is hermetically sealed. In the open configuration, the trap door is displaced from the container to form a fluid passage between the internal volume and a volume within the sterilization chamber that is external to the container. The mechanism is configured for selective reconfiguration of the trap door from the closed configuration to the open configuration. The mechanism is configured to automatically reconfigure the trap door from the open configuration to the closed configuration upon completion of a designated portion of a sterilization cycle for one or more surgical implements disposed within the internal volume.

In many embodiments, the container includes a base portion and a top cover that is attachable to and detachable from the base portion. One or more surgical implements can be placed into the base portion and then the top cover attached. The top cover can have an opening that is blocked by the trap door when the trap door is in the closed configuration. When in the open configuration, the trap door does not block the opening, thereby placing the internal volume of the container in fluid communication with the surrounding environment.

In many embodiments, the apparatus includes one or more spring elements that generate an interface force between the trap door and the top cover when the trap door is in the closed configuration. Such an interface force can ensure compression of an interface seal disposed between the trap door and the top cover, thereby serving to increase the effectiveness of the interface seal. In many embodiments, the one or more spring elements generate a force on the trap door that is reacted by the mechanism when the trap door is in the open configuration. In various embodiments, when the trap door is closed, a vacuum pressure or other condition may exist within the internal volume of the apparatus and provide an additional force that biases the trap door toward the closed configuration.

In many embodiments, the mechanism includes an actuation member and a latch device. The latch device may be mechanical, magnetic, or electromagnetic. The actuation member is configured to be manually displaced by a user to reconfigure the trap door from the closed configuration to the open configuration. The latch device is configured to maintain the trap door in the open configuration until after completion of the designated portion of the sterilization cycle and/or until environmental conditions within the internal volume satisfy certain criteria.

In many embodiments, the mechanism includes a temperature sensor, a pressure sensor, a solenoid, and a control unit. The temperature sensor can be configured to generate a temperature sensor output indicative of a temperature of the internal volume. The pressure sensor can be configured to generate a pressure sensor output indicative of the pressure within the internal volume. The solenoid can be coupled with the latch device and operable to unlatch the latch device so as to cause reconfiguration of the trap door from the open configuration to the closed configuration. The control unit can be configured to receive the temperature sensor and/or pressure sensor output and control the solenoid. The control unit can be configured to determine if conditions within the internal volume satisfy certain criteria (e.g., corresponding to the completion of the designated portion of the sterilization cycle) and in response to the criteria being satisfied, actuate the solenoid to unlatch the latch device, thereby causing the apparatus to reconfigure into the closed configuration.

Any suitable criteria can be used. For example, the control unit can actuate the solenoid based on the temperature of the internal volume being equal to or greater than a selected sterilization temperature for a suitable period of time and/or based on pressure in the internal volume reaching a predetermined level or a combination of criteria.

Any suitable latch device can be used. For example, the latch device can include a rotatable link that is rotatable by the solenoid from a latched orientation that maintains the trap door in the open configuration to an unlatched orientation that permits reconfiguration of the trap door from the open configuration to the closed configuration.

The trap door can be coupled with the container using any suitable means. For example, the trap door can include a plurality of apertures with each of the apertures being configured to receive and interface with a respective guide feature attached to the container so as to constrain movement of the trap door relative to the container between the closed configuration and the open configuration.

The trap door can be coupled with the actuation member using any suitable means. For example, the actuation member can be coupled with the trap door via a beam member mounted to rotate about a pivot point that is fixed relative to the container. The pivot point can be disposed between the trap door and the actuation member so that pressing the actuation member towards the container causes the trap door to be moved away from the container.

The actuation member can be coupled with the latch device so that movement of the actuation member can be used to engage the latch device. For example, the actuation member can be coupled with the latch device via a two-force link that is oriented transverse to a movement direction of the actuation member relative to the container for each of the open and closed configurations of the trap door.

Any suitable configuration of the latch device can be used. For example, the latch device can include a latch link constrained to linear translation relative to the container. The latch link can be driven via the two-force link between a latched position used to hold the trap door in the open configuration and a position for which the trap door is in the closed configuration. The latch link can have a cam surface and a recess. Movement of the latch link toward the latched position can result in engagement between a spring-biased latch member and the cam surface to position the latch member for engagement with the recess. Actuation of the solenoid can be used to drive the spring-biased latch member out of engagement with the recess, thereby permitting movement of the latch link from the latched position to the position for which the trap door is in the closed configuration.

In many embodiments, the latch device is operatively coupled with the trap door via a linkage. The linkage can react to the force generated on the trap door by one or more spring elements into the latch device when the trap door is in the open configuration.

The mechanism can employ mechanical components instead of electrical components. For example, the mechanism can include a mechanical thermostat and a mechanical timer. The mechanical thermostat can have a first configuration at a first temperature below a sterilization temperature and a second configuration at a second temperature equal to or greater than the sterilization temperature. A latch device can be operatively coupled with the mechanical thermostat and configured to block a timing operation of the mechanical timer when the mechanical thermostat is in the first configuration and permit the timing operation when the thermostat is in the second configuration. The mechanical timer can be coupled with the trap door via a linkage so as to maintain the trap door displaced from the container until expiration of a time period determined by the mechanical timer. For example, a user displacement of the actuation member can be used to translate a geared rack to engage and rotate a timer gear drivingly coupled with the mechanical timer so as to wind the mechanical timer to enable the mechanical timer to effect the timing operation. At the end of the timed period, the geared rack can become disengaged from the timer gear to permit reconfiguration of the trap door into the closed configuration.

For a fuller understanding of the nature and advantages of the present invention, reference should be made to the ensuing detailed description and accompanying drawing.

BRIEF DESCRIPTION OF THE DRAWINGS

FIG. 1 illustrates an apparatus for use in sterilizing items and storing the sterilized items therein prior to use, in accordance with many embodiments.

FIGS. 2 and 3 illustrate an actuation sequence of a mechanism portion of the apparatus of FIG. 1 between a closed configuration and an open configuration.

FIGS. 4, 5, and 6 are side views of the apparatus of FIG. 1 illustrating reconfiguration of a trap door between the closed configuration and the open configuration.

FIG. 7 illustrates acts of a method for sterilizing items and subsequent storage thereof prior to use, in accordance with many embodiments.

FIG. 8 illustrates acts of a method for reconfiguring an apparatus used to sterilize items and subsequent storage thereof prior to use between open and closed configurations, in accordance with many embodiments.

FIG. 9 illustrates acts of a method for controlling a solenoid used to reconfigure an apparatus used to sterilize items and subsequent storage thereof prior to use from an open configuration to a closed configuration following completion of a sterilization cycle, in accordance with many embodiments.

FIG. 10 illustrates acts of a method for monitoring the state of a hermetic sealed internal volume of an apparatus used to sterilize items and subsequent storage thereof prior to use, in accordance with many embodiments.

FIGS. 11, 12, and 13 illustrate an actuation sequence of a sterilization and storage apparatus employing a mechanical timer and a mechanical thermostat, in accordance with many embodiments.

FIG. 14A is a chart illustrating phases of a typical sterilization cycle according to various embodiments herein.

DETAILED DESCRIPTION

Figure 12:
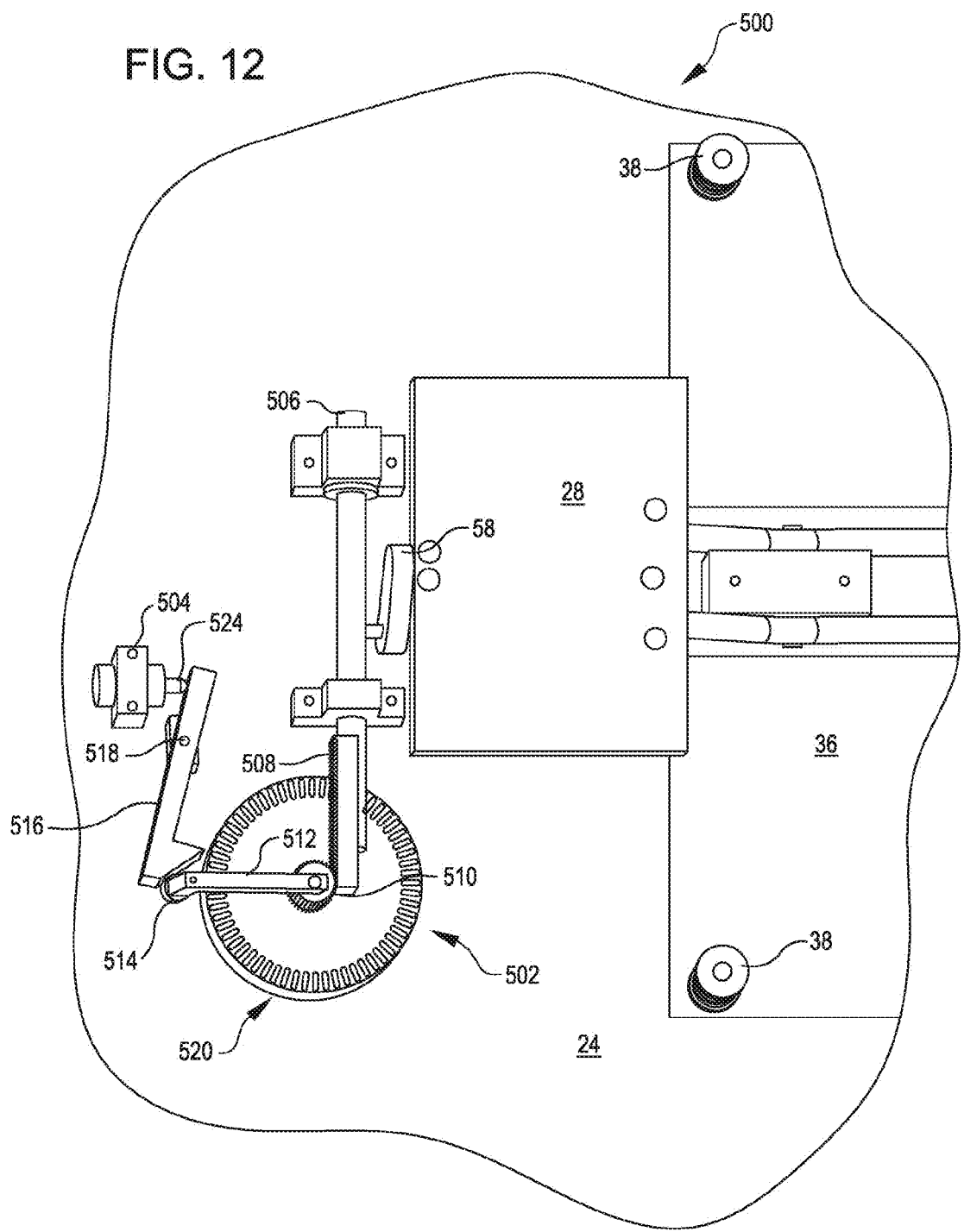

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Apparatus and related methods are described for sterilizing items (e.g., surgical instruments, instrument trays, implants, and/or implant trays) within a sterilization chamber and subsequent transportation and/or storage of the sterilized items prior to use. For example, a filter-less, reusable sterilization apparatus is described that in an initial configuration (open configuration) provides a pathway to allow the flux of gases (e.g., air, water vapor, etc.) into and out of the apparatus. The apparatus includes a temperature-sensing component, a pressure-sensing component, a humidity-sensing component, and/or a timer, which work together to initiate a reconfiguration of the apparatus to a closed configuration in which the apparatus is hermetically sealed. In many embodiments, the temperature-sensing component monitors temperature of the gases surrounding and/or within the apparatus until a target temperature is reached (e.g., a selected sterilization temperature for sterilizing items within the apparatus). Once the target temperature is reached, the apparatus becomes sensitive to the environmental pressure and/or humidity. Once the environmental pressure and/or humidity reaches a desirable level (e.g., sub-atmospheric and/or low humidity), the pressure sensor initiates reconfiguration of the apparatus into the closed configuration, thereby disrupting the gas pathway and stopping the flux of gases into or out of the apparatus. The apparatus can be kept in the closed configuration and will maintain the environment established within the apparatus at the time the reconfiguration of the apparatus and disruption of the gas pathway (e.g., a sub-atmospheric pressure and/or low humidity state) through a hermetic seal until the contents of the apparatus are accessed for use. When access to the contents of the apparatus is required, the apparatus may either be restored to its initial (open) configuration, which will allow access to the contents directly through the pathway described above, or the apparatus may be put into a third configuration to provide access (e.g., the apparatus's lid is removed).

Referring now to the drawings, in which like reference numerals represent like parts throughout the several views, FIG. 1 shows an apparatus 10 for use in sterilizing items and storing the sterilized items therein prior to use, in accordance with many embodiments. The apparatus 10 includes a base portion 12 and a top cover assembly 14.

The base portion 12 is configured to receive and hold items to be sterilized. In the illustrated embodiment, the base portion 12 has a lower surface 16 and four side walls 18. The lower surface 16 and the four side walls 18 form a fluid-tight open-ended container having a circumferential upper edge 20. The upper edge 20 is configured to sealingly interface with the top cover assembly 14, thereby defining an internal volume that can be hermetically sealed to store sterilized items prior to use.

The top cover assembly 14 is attachable to and detachable from the base portion 12. In many embodiments, the top cover assembly 14 includes a perimeter seal 22 configured to sealingly interface with the upper edge 20 of the base portion 12. In use, items to be sterilized can be placed into the base portion 12 prior to attachment of the top cover assembly 14 to the base portion 12.

The top cover assembly 14 includes a top cover base 24, a trap door assembly 26, an actuation member 28, a latch device 30, a solenoid 32, and a control unit 34. The top cover base 24 provides a base that supports the perimeter seal 22, the trap door assembly 26, the latch device 30, the solenoid 32, and the control unit 34. FIG. 1 shows the apparatus in a closed configuration in which the top cover base 24 and the trap door assembly 26 form a hermetically sealed barrier, which when coupled with the base portion 12 form a hermetically sealed internal volume for storing sterilized items prior to use.

The trap door assembly 26 includes a trap door 36 and spring-loaded mounts 38 by which the trap door 36 is coupled with the top cover base 24. Each of the spring-loaded mounts 38 interfaces with a respective aperture through the trap door 36 to constrain motion of the trap door 36 relative to the top cover base 24. Each of the spring-loaded mounts 38 also interfaces with a top surface area surrounding the respective aperture to exert a force onto the trap door 36 that presses on the trap door 36 towards the top cover base 24. In the closed configuration illustrated in FIG. 1, the forces exerted by the spring-loaded mounts 38 onto the trap door 36 serves to compress an interface seal disposed between the trap door 36 and the top cover based 24, thereby forming a hermetic seal between the trap door 36 and the top cover base 24.

Reconfiguration of the top cover assembly 14 between the closed configuration and an open configuration will now be described with reference to FIG. 2 through FIGS. 6. To reconfigure the top cover assembly 14 to the open configuration, the actuation member 28 is pressed towards the top cover base 24 (i.e., in direction 40). The actuation member 28 is attached to a pivot beam assembly 42, which lifts the trap door 36 away from the top cover base 24 as a result of motion of the actuation member 28 towards the top cover base 24. The pivot beam assembly 42 includes a pair of pivot beams 44, which are pivotally connected with a pivot block 46 for rotation relative to the pivot block 46 about a pivot axis 48. The pivot block 46 is rigidly attached to the top cover base 24. The resulting pivoting of the pivot beams 44 about the pivot axis 48 results in the pivot beams 44 exerting a lifting force on a lifting fitting 50 attached to the trap door 36, thereby lifting the trap door 36 away from the top cover base 24, compressing the springs of the spring-loaded mounts 38, and exposing an opening 52 in the top cover base 24. FIG. 4 shows a side view of the trap door 36 in the closed configuration. FIG. 6 shows a side view of the trap door 36 in the open configuration. And FIG. 5 shows a side view of the trap door 36 in an intermediate configuration between the open and closed configurations.

The latch device 30 is configured to retain the trap door 36 in the open configuration illustrated in FIG. 3 and in FIG. 6 until being disengaged via actuation of the solenoid 32. The latch device 30 includes a latch link 54 and a spring-loaded toggle link 56. The latch link 54 is mounted to the top cover base 24 so as to be constrained to linear translation with no rotation relative to the top cover base 24. A two-force link 58 drivingly connects the actuation member 28 to the latch link 54. In the closed configuration (FIG. 2 and FIG. 4), the two-force link 58 is oriented at an angle relative to a plane normal to the translation direction of the latch link 54. As a result, when the actuation member 28 is pressed towards the top cover base 24, the resulting compression in the two-force link 58 imparts a force component onto the latch link 54 in the translation direction of the latch link 54. The imparted force component causes the latch link 54 to translate from the position of the latch link 54 for the closed configuration of the trap door 36 shown in FIG. 1 and FIG. 2 to the position of the latch link 54 for the open configuration of the trap door shown in FIG. 3. One end of the latch link 54 has a cam surface 60 and a recess 62. The spring-loaded toggle link 56 includes a roller 64 that engages the cam surface 60 when the trap door 36 is in the closed configuration and is received by recess 62 when the trap door 36 is moved to the open configuration. The spring-loaded toggle link 56 is pivotally mounted to the top cover base 24 via a pivot mount 66. A tension spring 68 is connected at one end to the toggle link 56 and at the other end to the top cover base 24, thereby biasing rotation of the toggle link 56 towards contact between the roller 64 and the latch link 54 (e.g., with the cam surface 60 or the recess 62 depending on the position of the trap door 36 relative to the top cover base 24). Translation of the latch link 54 as a result of movement of the actuation member 28 towards the top cover base 24 results in rotation of the toggle link 56 as the roller 64 rolls along the cam surface 60. Further translation of the latch link 54 serves to position the recess 62 to receive the roller 64 via rotation of the toggle link 56 induced by the tension spring 68. Once received within the recess, the toggle link 56 reacts forces applied to the trap door 36 by the spring-loaded mounts 38, thereby retaining the trap door 36 in the open configuration.

The solenoid 32 is configured to controllably rotate the toggle link 56 so as to remove the roller 64 from the recess 62, thereby no longer preventing translation of the latch link 54. Once the latch link 54 is free to translate the forces applied to the trap door 36 by the spring-loaded mounts 38 are no longer reacted into the toggle link 56 via the pivot beam assembly 42, the actuation member 28, the two-force link 58, and the latch link 54; as a result, the trap door 36 transitions from the open configuration to the closed configuration.

Actuation of the solenoid 32 is controlled by the control unit 34. The control unit 34 includes a temperature sensor that is configured to output one or more signals indicative of the temperature inside the interior volume of the apparatus 10 and/or the temperature surrounding the apparatus 10. In many embodiments, the control unit 34 includes control electronics that monitor the temperature sensor output(s) to identify when the measured temperature(s) are equal to or greater than a selected temperature for sterilizing items within the apparatus 10 and to actuate the solenoid 32 after a target period of time and/or when particular environmental conditions within the apparatus and/or autoclave exist (e.g., a duration of time required to sterilize apparatus contents, and optionally an additional duration of time to achieve desirable environmental conditions within the apparatus). Once the target period of time has passed or particular environment conditions exist, the control unit 34 actuates the solenoid 32 to reconfigure the apparatus 10 into the closed configuration, thereby disrupting the gas pathway and stopping the flux of gases into or out of the apparatus 10. The apparatus 10 can then be maintained in the closed configuration until the sterilized items within the apparatus 10 are accessed for use. While the sterilization cycle described is based on the passing of a target period of time, the point at which the solenoid is actuated can be based on any suitable approach, such as by using the temperature sensor to track the actual temperature profile over time within the interior volume of the apparatus 10 and determining a total sterilization time based on the measured actual temperature profile.

In many embodiments, the control unit 34 includes a pressure sensor that outputs a pressure signal indicative of the internal pressure of the interior volume of the apparatus 10. The control unit 34 can monitor the pressure signal to detect the pressure within the interior volume of the apparatus 10 during the sterilization cycle. After the apparatus 10 is reconfigured to the closed (hermetically sealed) configuration within a sterilization chamber (e.g., autoclave), the environmental conditions within the apparatus 10 at the time it is reconfigured into the closed configuration will remain until the hermetic seal is broken. For example, a pressure differential between the interior and exterior volume of the apparatus may exist as a result of the interior volume of the apparatus remaining below the pressure of the exterior volume at the conclusion of the sterilization cycle. Without significant entry of air into the apparatus 10, the pressure within the apparatus 10 will remain below the surrounding atmospheric pressure. Therefore, the apparatus 10 can utilize the pressure sensor signal to indicate the loss of hermetic seal and can trigger one or more indicators controlled by the control electronics 34 that are used to indicate whether: (1) the interior pressure of the apparatus 10 is below the surrounding atmospheric pressure, thereby indicating retention of the hermetic seal; and (2) the interior pressure of the apparatus is not below the surrounding atmospheric pressure, thereby indicating possible loss of the hermetic seal. For example, a green indicator light (e.g., a green light emitting diode (LED)) can be lit to indicate that the interior pressure of the apparatus 10 is below the surrounding atmospheric pressure. And the green indicator light can be turned off and/or a red indicator light can be lit to indicate that the interior pressure of the apparatus 10 is not below the surrounding atmospheric pressure. In some embodiments, pressure indicators used to demonstrate integrity of the hermetic seal might additionally or alternatively be mechanical.

The functionality described above may be achieved by use of electronics such as microcontrollers or hard logic. A microcontroller can be a small computer on a single integrated circuit containing a processor core, memory, and programmable input/output peripherals. Microcontrollers can be designed for embedded applications, in contrast to the microprocessors used in personal computers or other general purpose applications. Microcontrollers can be used in automatically controlled products and devices. By reducing the size and cost compared to a design that uses a separate microprocessor, memory, and input/output devices, microcontrollers make it economical to digitally control many devices and processes. Hard logic can include a combination of electrical components that are operatively connected and designed to perform one or more specific tasks. In contrast, a microcontroller is programmable enabling the ability to perform different tasks by changing the programming code and uploading the programming code to the microcontroller. Sterilization apparatuses described herein can use such electronics to perform related functionality described herein including, but not limited to, reading a continuous signal from a temperature sensor, determining when the sensed temperature is equal to or greater than a predetermined target temperature, initiating a timer, and actuating a solenoid after an elapsed period of time to reconfigure a sterilization apparatus into a closed, hermetically-sealed, configuration.

FIG. 7 shows acts of a method 100 of sterilizing surgical implements and storing the sterilized surgical instruments prior to use, in accordance with many embodiments. Any suitable sterilization apparatus described herein can be used to accomplish the method 100.

In acts 102 through 106, the sterilization apparatus is prepared for placement into a sterilization chamber. In act 102, items to be sterilized are placed into the base portion of a sterilization apparatus, for example, any of the sterilization apparatuses described herein. The items to be sterilized that are placed into the base portion of the sterilization apparatus can include any suitable item, such as, for example, surgical instruments, surgical instrument trays, surgical implants, and/or surgical implant trays. In act 104, the top cover assembly is attached to the base portion and secured. In act 106, the sterilization apparatus is reconfigured to place the trap door into the open configuration.

In acts 108 through 122, a sterilization chamber is used to sterilize the items placed within the sterilization apparatus. In act 108, the sterilization chamber, with the trap door in the open configuration, is placed within a sterilization chamber and the sterilization chamber is turned on, thereby causing the temperature within the sterilization chamber to increase towards a target sterilization temperature or sterilization temperature profile for the sterilization chamber. In act 110, a determination is made that the temperature inside the sterilization apparatus and/or within the sterilization chamber has reached a selected sterilization temperature (e.g., 276 degrees F.). For example, where the sterilization apparatus includes a temperature sensor and an electronic control unit that receives an output of the temperature sensor, the control electronics can monitor the temperature sensor output to determine when the sensed temperature has reached the selected sterilization temperature. As another example, the sterilization apparatus can include a mechanical temperature device, such as a mechanical thermostat, that is used to determine when the sensed temperature has reached the selected sterilization temperature. In act 112, once the selected sterilization temperature is reached, a sterilization timer is started. In act 114, the sterilization timer tracks elapsed time to ensure that the items are subjected to the elevated temperature for a sufficient period of time to sterilize the items. For example, with a selected sterilization temperature of 276 degrees F., the sterilization time period can be set to be greater than or equal to ten minutes. At the end of the sterilization time period and/or when particular environmental conditions exist, the sterilization apparatus is automatically reconfigured to the closed (hermetically sealed) configuration (act 116). In act 118, the sterilization chamber cycle ends. In act 120, the sealed sterilization apparatus is removed from the sterilization chamber.

The sealed sterilization apparatus can then be stored prior to use of the sterilized items stored within the sterilization apparatus (act 122). When needed, the sterilization apparatus can be brought to a location where the sterilized items are to be removed from the sterilization apparatus (act 124). Once at the use location (e.g., once in a sterile field in an operating room), the top cover assembly of the sterilization apparatus can be removed, thereby breaking the vacuum seal, and the sterilized items removed for use (act 126).

FIG. 8 shows acts of a method 200 for reconfiguring a sterilization apparatus used to sterilize items and subsequent storage thereof prior to use between open and closed configurations, in accordance with many embodiments. Any suitable sterilization apparatus described herein can be used to accomplish the method 200. The method 200 can be repeated any suitable number of times, for example, to sterilize and store additional items.

In acts 202 through 206, the sterilization apparatus is reconfigured from the closed configuration to the open configuration. In act 202, an actuation member operatively coupled with a trap door is depressed (act 202). As a result, the trap door moves away from the top cover base, thereby opening an air passageway between the interior volume of the sterilization apparatus and the surrounding of the sterilization apparatus (act 204). The movement of the actuation member also produces movement of a latch link to a latched position where it is held in place, thereby serving to hold the trap door in the open configuration (act 206). With the trap door in the open configuration, the sterilization apparatus can be placed into a sterilization chamber and the sterilization chamber turned on.

In acts 208 through 212, the sterilization apparatus is reconfigured from the closed configuration to the open configuration. With the sterilization chamber turned on and heating up, the sterilization apparatus detects when the temperature within the sterilization apparatus and/or within the sterilization chamber reaches a predetermined temperature (e.g., a selected sterilization temperature) and initiates a sterilization timer, which tracks elapsed time to ensure that the items within the sterilization apparatus are subjected to the sterilization temperature for a sufficient period of time to sterilize the items. Once the elapsed time reaches a predetermined time threshold and/or once particular environmental conditions exist within the interior volume of the apparatus, the latch link is unlatched (e.g., a solenoid is actuated to unlatch the latch link) (act 208). As a result, the latch link is released (act 210). With the latch link released, the sterilization apparatus reconfigures to a closed configuration where the trap door is closed, thereby hermetically sealing the sterilized items within the sterilization apparatus (act 212).

FIG. 9 shows acts of a method 300 for controlling a solenoid used to trigger reconfiguration of a sterilization apparatus from an open configuration to a closed configuration, in accordance with many embodiments. The method 300 can be repeated any suitable number of times, for example, as part of a process to sterilize and store additional items.

The method 300 can be accomplished using any suitable sterilization apparatus, for example, using the sterilization apparatus 10 described herein. In act 302, a signal from a temperature sensor is read to determine the current temperature sensed by the temperature sensor (e.g., the temperature inside the sterilization apparatus and/or the temperature within the sterilization chamber). Act 302 is repeated on a regular basis to continually monitor the temperature sensed by the temperature sensor. Once the temperature sensed by the temperature sensor is greater than a predetermined value (e.g., a selected sterilization temperature, for example, 276 degrees F.) a countdown timer is started (e.g., a signal is sent to a countdown timing chip or a microcontroller with a timing chip to commence a countdown of a predetermined time duration) (act 304). The apparatus is kept in the open configuration while the countdown timer counts down for the predetermined time duration, which can be selected to ensure that the items within the sterilization apparatus are subjected to the sterilization temperature for a sufficient period of time to sterilize the items (act 306). For example, the predetermined time duration can be greater than or equal to ten minutes. Once the predetermined time duration has elapsed and/or once particular environmental conditions exist within the interior volume of the apparatus, a signal is sent to actuate the solenoid so as to reconfigure the sterilization apparatus from the open configuration to the closed configuration (act 308). Upon removal of the sterilization apparatus from the sterilization chamber, the temperature sensed by the temperature sensor reduces. Once the temperature sensed by the temperature sensor reduces below a reset temperature value (e.g., a suitable temperature such as room temperature or a temperature a suitable margin above room temperature), the logic of the control unit accomplishing the method 300 can be reset, thereby preparing the control unit to accomplish another iteration of the method 300.

Although the method 300 is described above as monitoring time, other criteria may be monitored additionally or alternatively. In some embodiments, pressure or some other environmental condition (instead of time) is monitored when the temperature reaches the predetermined value. For example, once a particular temperature is indicated, a detection of a subsequent low or sub-atmospheric pressure and/or low humidity state may cause triggering of the apparatus to reconfigure the sterilization apparatus from the open configuration to the closed configuration. In some aspects, this functionality correlates to the sterilization process of an autoclave that is configured to maintain a temperature at high or supra-atmospheric pressure for a configured duration of time and then (upon achieving those time, temperature and/or pressure requirements) shift to a lower temperature, vacuum state.

FIG. 10 shows acts of a method 400 for monitoring the state of seal of a sterilization apparatus used to sterilize and store sterilized items prior to use, in accordance with many embodiments. The method 400 can be repeated any suitable number of times, for example, as part of a process to sterilize and store additional items.

The method 400 can be accomplished using any suitable sterilization apparatus, for example, using the sterilization apparatus 10 described herein. In act 402, a signal from an electronic pressure sensor configured to sense the pressure inside a sterilization apparatus is read and processed to determine the current pressure inside the sterilization apparatus. In many embodiments, a signal from an electronic pressure sensor configured to sense the atmospheric pressure outside the sterilization apparatus is also read and processed to determine the current atmospheric pressure outside the sterilization apparatus. A comparison is made to determine if the current pressure inside the sterilization apparatus is less than atmospheric pressure (act 404). For example, the measured pressure inside the sterilization apparatus can be compared to a measured pressure outside the sterilization apparatus or to a predetermined value for atmospheric pressure. If the pressure inside the sterilization apparatus is less than atmospheric pressure, a visual indicator (e.g., a green light emitting diode (LED)) can be lit (act 406). If the pressure inside the sterilization apparatus is not less than atmospheric pressure, the visual indicator can be turned off. Any suitable indication means can be employed such as, for example, any suitable visual and/or audible indication. The method 400 can be repeated on a regular basis to continually monitor the state of seal of a sterilization apparatus storing sterilized items prior to use.

Figure 13:
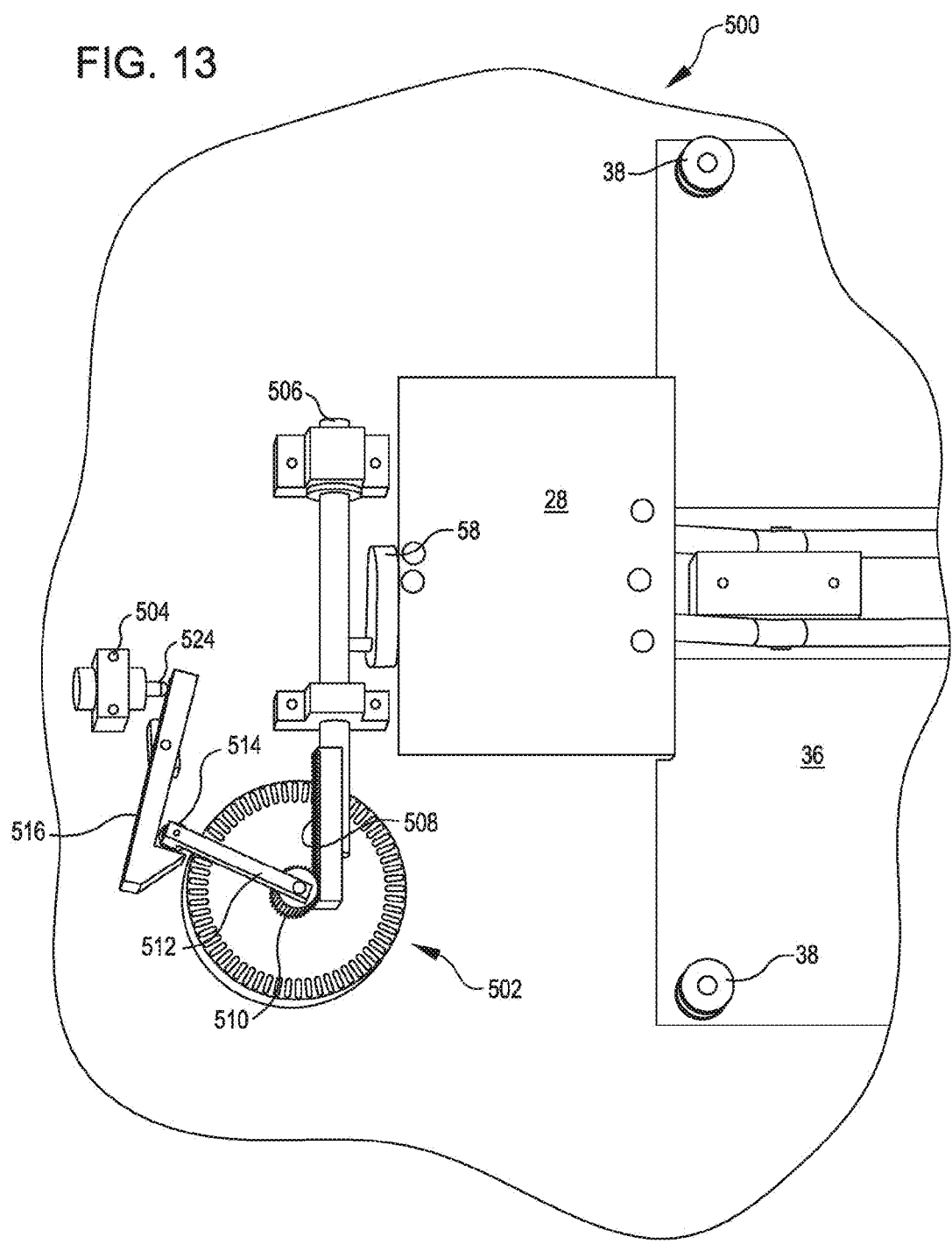

FIGS. 11, 12, and 13 illustrate an actuation sequence of a sterilization and storage apparatus 500 employing a mechanical timer 502 and a mechanical thermostat 504, in accordance with many embodiments. The apparatus 500 is similar to the apparatus 10, but employs a latch mechanism using the mechanical timer 502 and the mechanical thermostat 504. Accordingly, only the components of the apparatus 500 that are different from the corresponding components of the apparatus 10 are described. Any components that are the same are labeled with the same references numbers.

The mechanical timer 502 uses mechanical clockwork to measure time. Analogous manual timers are typically set by turning a dial to the time interval desired; turning the dial stores energy in a mainspring to run the mechanism. The energy in the mainspring causes a balance wheel to rotate back and forth. Each swing of the wheel releases the gear train to move forward by a small fixed amount, causing the dial to move steadily backward until it reaches zero.

FIG. 11 is a partial view of the apparatus 500 in the closed configuration. The apparatus 500 includes a latch link 506. The latch link 506 is mounted to the top cover base 24 so as to be constrained to linear translation with no rotation relative to the top cover base 24. A geared rack 508 is rigidly attached to one end of the latch link 506. The geared rack 508 has gear teeth configured to interface with a pinion gear 510 that is attached to the mechanical timer 502. In the closed configuration illustrated in FIG. 11, the latch link 506 is positioned such that a gap exists between the geared rack 508 and the pinion gear 510.

The two-force link 58 drivingly connects the actuation member 28 to the latch link 506. In the closed configuration (FIG. 11), the two-force link 58 is oriented at a non-zero angle relative to a plane normal to the translation direction of the latch link 506. As a result, when the actuation member 28 is pressed towards the top cover base 24, the resulting compression in the two-force link 58 imparts a force component onto the latch link 506 in the translation direction of the latch link 506. The imparted force component causes the latch link 506 to translate from the position of the latch link 506 for the closed configuration of the trap door 36 shown in FIG. 11 to subsequent positions of the latch link 506 shown in FIG. 12 and FIG. 13.

FIG. 12 shows the apparatus 500 in an intermediate configuration between the closed configuration (FIG. 11) and the open configuration (FIG. 13). From the closed configuration to the intermediate configuration, the motion of the actuation member 28 and the connected two-force link 58 translates the latch link 506 such that the gear rack 508 comes into engagement with the pinion gear 510 and rotates the pinion gear 510, thereby rotating the timer 502. A detent arm 512 is attached to the pinion gear 510 and rotates therewith. A detent roller 514 is rotatably attached to the detent arm 512. In the intermediate configuration illustrated, the translation of the latch link 506 has rotated the pinion gear 510, the timer 502, and the detent arm 512 to an angular orientation in which the detent roller 514 is engaged with a latch member 516.

The latch member 516 is rotatably mounted to the top cover base 24 to rotate about a pivot point 518. In many embodiments, the latch member 516 is mounted to the top cover base 24 so as to be rotatably biased toward contact with a perimeter surface 520 of the timer 502. For example, a torsional spring can be connected between the latch member 516 and the top cover base 24 to rotatably bias the latch member 516 into contact with the perimeter surface 520. The latch member 516 has a cam surface 522 configured to interface with the detent roller 514 and shaped such that movement of the detent roller 514 in response to movement of the latch link 506 induces rotation of the latch member 516 about the pivot point 518.

Further movement of the actuation member 28 towards the top cover base 24 is used to reconfigure the apparatus 500 from the intermediate configuration illustrated in FIG. 12 to the open and latched configuration illustrated in FIG. 13. The further movement of the actuation member 28 induces a corresponding further translation of the latch link 506; which induces a corresponding additional rotation of the mechanical timer 502, the pinion 510, and detent arm 512; which induces a corresponding additional movement of the detent roller 514, which induces rotation of the detent arm 516 via engagement of the cam surface 520 with the detent roller 514. After the detent roller 514 moves beyond the cam surface 520, the detent arm 516 rotates to capture the detent roller 514 as illustrated in FIG. 13. After the detent roller 514 is captured by the detent arm 516, the actuation member 28 can be released and the apparatus 500 will remain in the open configuration until unlatched via the action of the detent arm 516 and react the forces applied by the spring-loaded mounts 38 via the interconnecting linkage.

The apparatus 500, in the open configuration illustrated in FIG. 13, can then be placed into a sterilization chamber and the sterilization chamber turned on. The resulting increase in temperature induces a configuration change to the mechanical thermostat 504. The mechanical thermostat 504 is configured to extend a plunger 524 towards the detent arm 516 in response to increased temperature so as to rotate the detent arm 516 out of engagement with the detent roller 514 at a desired temperature level (e.g., at a selected sterilization temperature, for example, 276 degrees F.). When the detent roller 514 is no longer constrained by the detent arm 516, the mechanical timer 502 begins to operate and slowly rotate from the angular orientation shown in FIG. 13 to the angular orientation shown in FIG. 12 and finally to an angular rotation in which the geared rack 508 becomes disconnected from the pinion gear 510, thereby releasing the trap door 36 to the closed configuration and sealing the sterilized items within the apparatus 500.

Further Features

Figure 14:
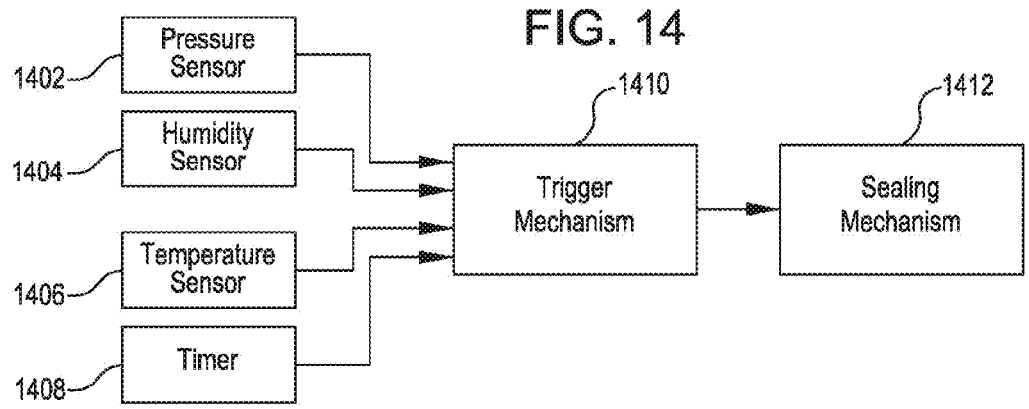
FIG. 14 is a block diagram illustrating elements of an apparatus according to various embodiments herein.

Subsequent figures presented herein illustrate further embodiments that are grouped together under additional sub-headings for the ease of the reader. In general, various embodiments correspond to the elements set forth in FIG. 14. Such an apparatus includes a sealing mechanism 1412 (such as a trap door) that includes at least one component that can be moved into and/or out of sealing engagement to change the apparatus between the open configuration and the closed configuration. A triggering mechanism 1410 causes the movement of the sealing mechanism 1412. The triggering mechanism 1410 initiates the movement in response to one or more inputs, such as a pressure sensor 1402, humidity sensor 1404, temperature sensor 1406, timer 1408, other sensor(s) for detecting an environmental condition within a sterilization chamber, or a combination thereof. In this way, the apparatus can function as a self- or automatically-sealing sterilization tray.

As additional context, the chart in FIG. 14A represents a typical pressure progression that exists inside a sterilization tray as the tray is subjected to a standard, pre-vacuum sterilization cycle. For the convenience of the reader, the chart is provided with a time axis and a pressure axis. The pressure axis reflects discrete values in multiples of atmospheric pressure, and the time axis is shown with an arbitrary time scale ranging from 0 to 150. Although such values may be representative of certain instances of sterilization cycles, it should also be understood that other scales, durations, magnitudes, units, etc. may be used in other relevant sterilization cycles. Referring to the solid line in the chart in FIG. 14A, during a sterilization phase 1412 (e.g., from time point, T20 to T55), the chamber generates a series of pressure-vacuum pulses 1418. Immediately following the pre-evacuation phase 1410 and the associated pressure-vacuum pulses 1418, the chamber initiates the sterilization phase 1412 (e.g., at T55), which entails an escalation or ramping 1420 of the pressure, humidity and temperature until the temperature reaches a target sterilization temperature (e.g., at T70). Pressure, temperature, and humidity are held for a target period 1422 of time deemed suitable for achieving sterilization of contents of the chamber. After the sterilization phase 1412, the chamber initiates a drying phase 1414 (e.g., at T85), which begins by a decrease 1424 of pressure for drawing of a vacuum. The vacuum is maintained at an elevated temperature (e.g., greater than room temperature) in the absence of any injected water vapor/humidity for an additional target period 1426 of time. After the drying phase 1414, the chamber proceeds to a post-drying phase 1416 (e.g., at T100). The post-drying phase 1416 typically begins with a pressure increase 1428 for returning the chamber to atmospheric pressure. Upon reaching atmospheric pressure the chamber may be opened to allow the contents to cool before subsequent transport and/or use. (Some chambers prior to opening in the post-drying phase 1416 may be configured to perform additional operations such as further vacuum pulses (e.g., as illustrated in dotted line at 1430), but such variations are well known and not discussed in further detail here.)

In various embodiments, a self-sealing sterilization tray can respond to pressure and/or maintain conditions introduced during the sterilization cycle. For example, in the graph of FIG. 14A, the charted pressure signals may illustrate a difference between a pressure measured inside a standard sterilization tray (solid line) and a self-sealing tray (dashed line). Any instruments placed inside either tray will experience the same conditions through the sterilization phase 1412. However, the standard tray and the self-sealing tray may experience different conditions as early as the drying phase 1414. For example, in various embodiments herein, a self-sealing tray may be configured to close some time after the chamber reaches a specific sub-atmospheric pressure during the decrease 1424 in pressure that occurs at the transition between the sterilization phase 1412 and the drying phase 1414. In some embodiments, the relevant specific sub-atmospheric pressure may be the sub-atmospheric pressure at which the chamber is maintained during the drying phase 1414 (e.g., the tray may seal when a pressure in the chamber ceases decreasing for a period of time), or the relevant specific sub-atmospheric pressure may be some other sub-atmospheric pressure, such as a pressure that is a certain amount below atmospheric pressure. In some embodiments, the self-sealing trays may seal immediately upon reaching such a specific sub-atmospheric pressure or within a certain time threshold thereafter. In some embodiments, the self-sealing trays may seal in response to detecting particular environmental conditions, which may include particular values for pressure, humidity, temperature, and/or other criteria. Upon sealing, a self-sealing tray may hold the vacuum or other conditions present at sealing for an ongoing and/or unspecified amount of time that may extend until the tray is unsealed for use (e.g., regardless of subsequent changes to conditions in the chamber). In contrast, the pressure and environment within the standard tray will follow the conditions of the chamber. This is demonstrated in the chart of FIG. 14A by the pressure within the standard tray returning to atmospheric pressure (e.g., the solid line at T110 rises to 1 ATM) while the self-sealing tray does not undergo the same shift (e.g., the dashed line remains at approximately 0.1 ATM through and beyond T110). As a result, the self-sealing tray may maintain instruments contained therein in a low pressure state until use, unlike the standard tray.

Electro-Magnetic Sealing Mechanisms

Figure 15:
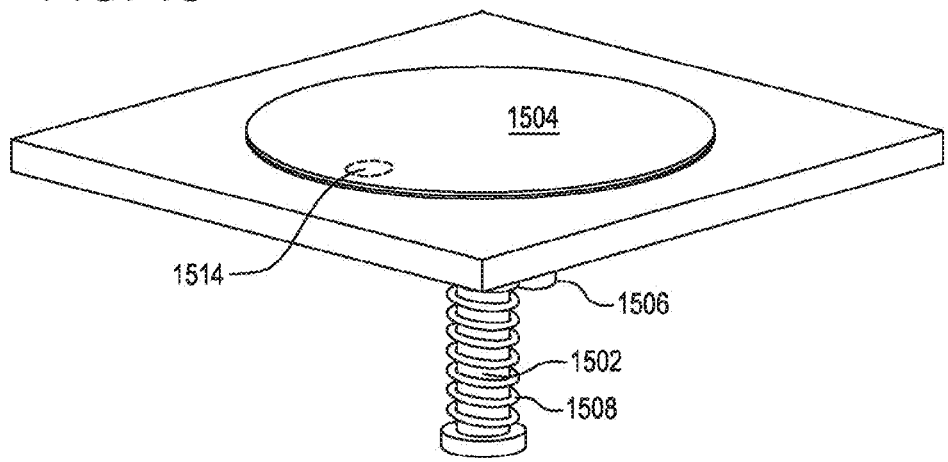
FIGS. 15, 16, and 17 illustrate a first example of an electro-magnetic sealing mechanism, in accordance with many embodiments.
Figure 16:
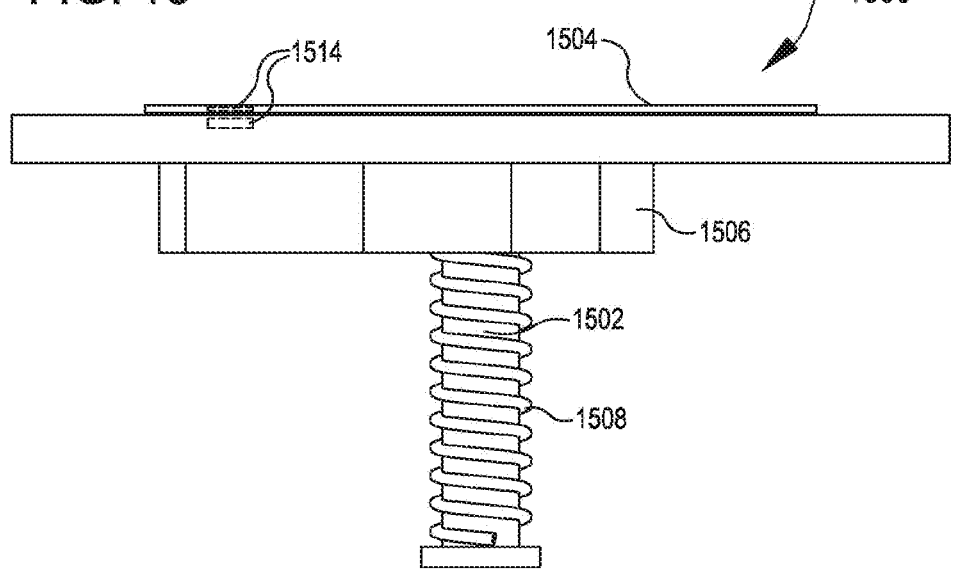
Figure 17:
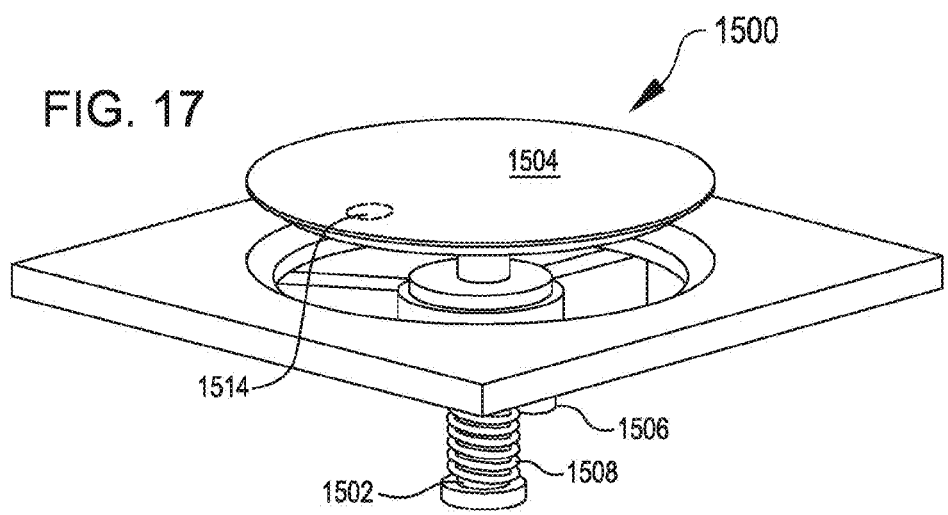
Figure 18:
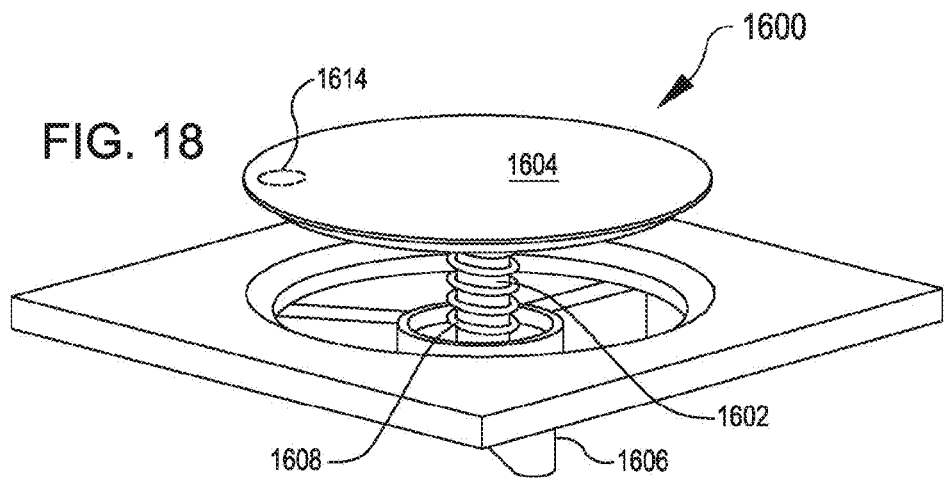
FIGS. 18, 19, 20, and 21 illustrate another example of an electro-magnetic sealing mechanism, in accordance with many embodiments.
Figure 19:
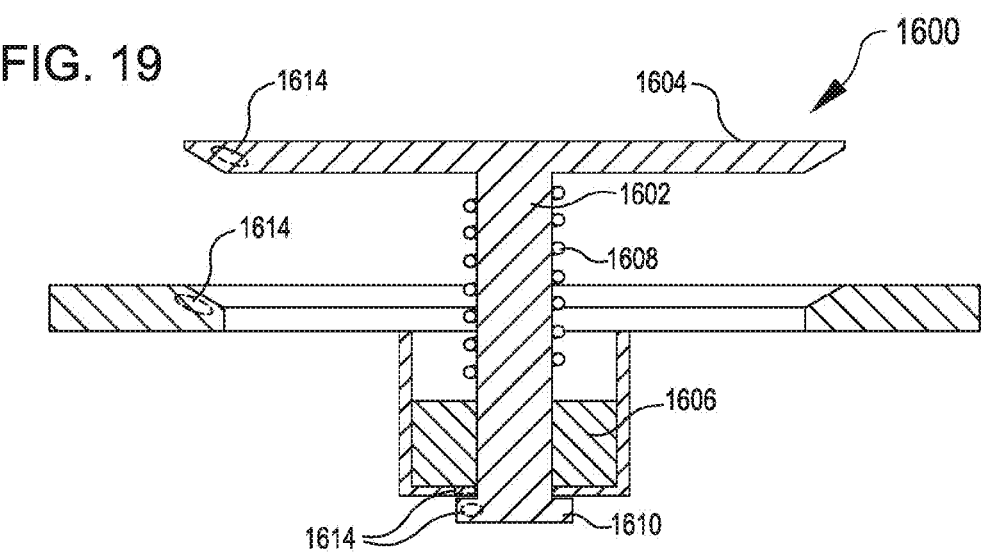
Figure 20:
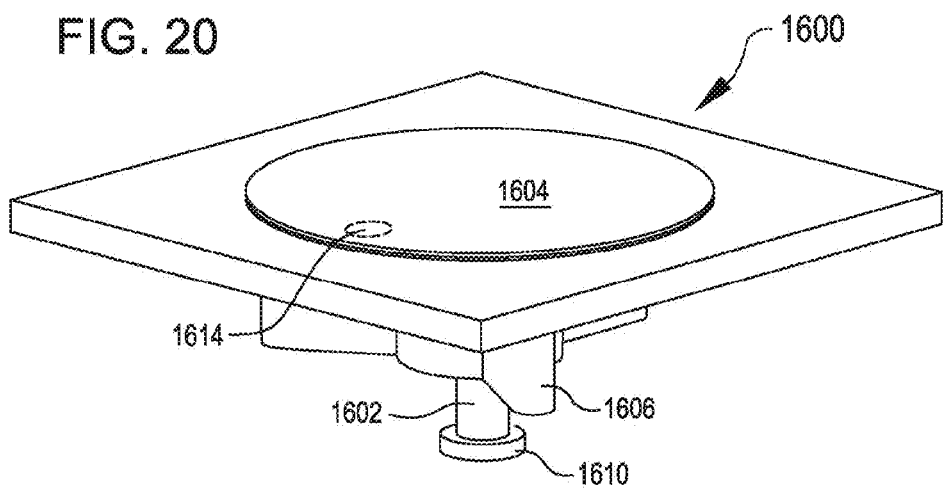
Figure 21:
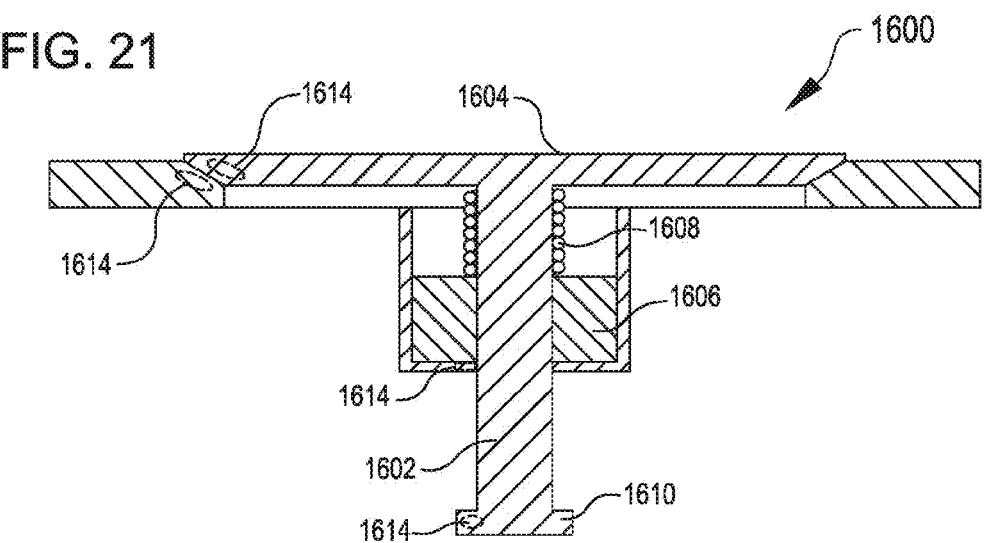
Figure 22:
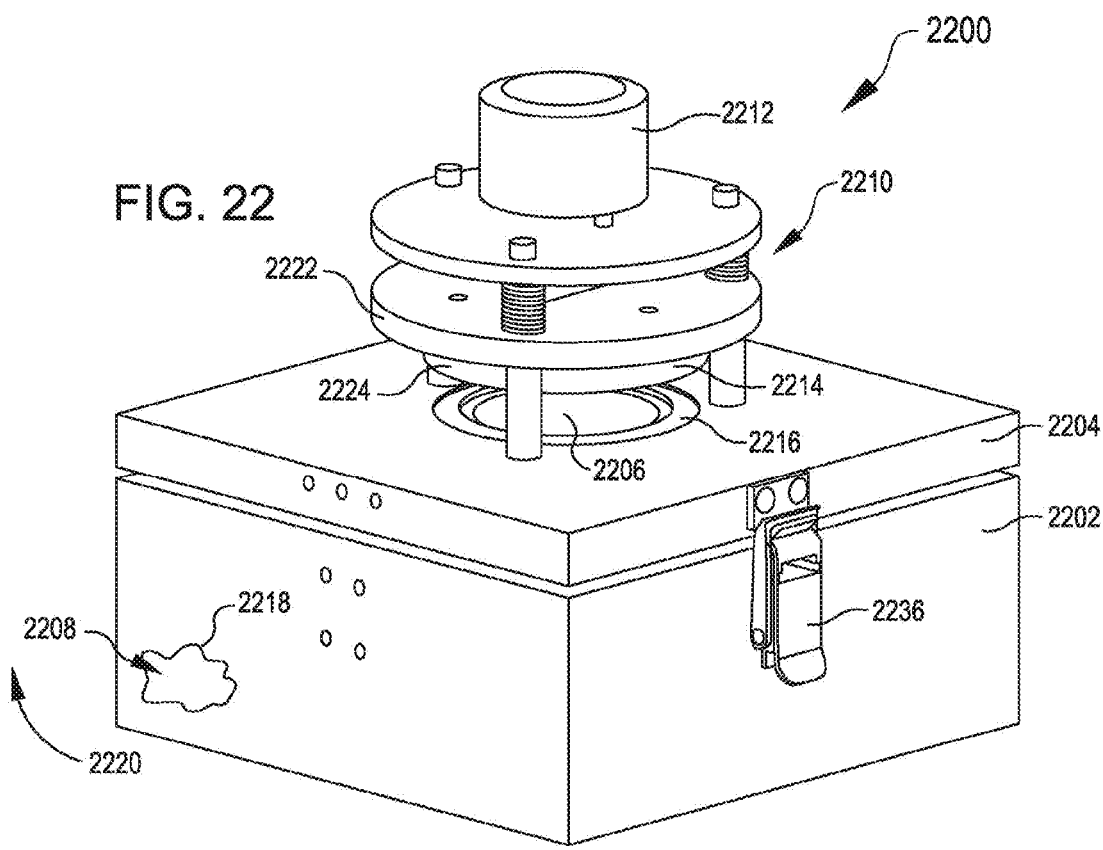
FIGS. 22, 23, 24, 25, 26, 27, 28, 29, 30, 31, and 32 illustrate another embodiment of a self-sealing sterilization tray, in accordance with many embodiments.
Figure 23:
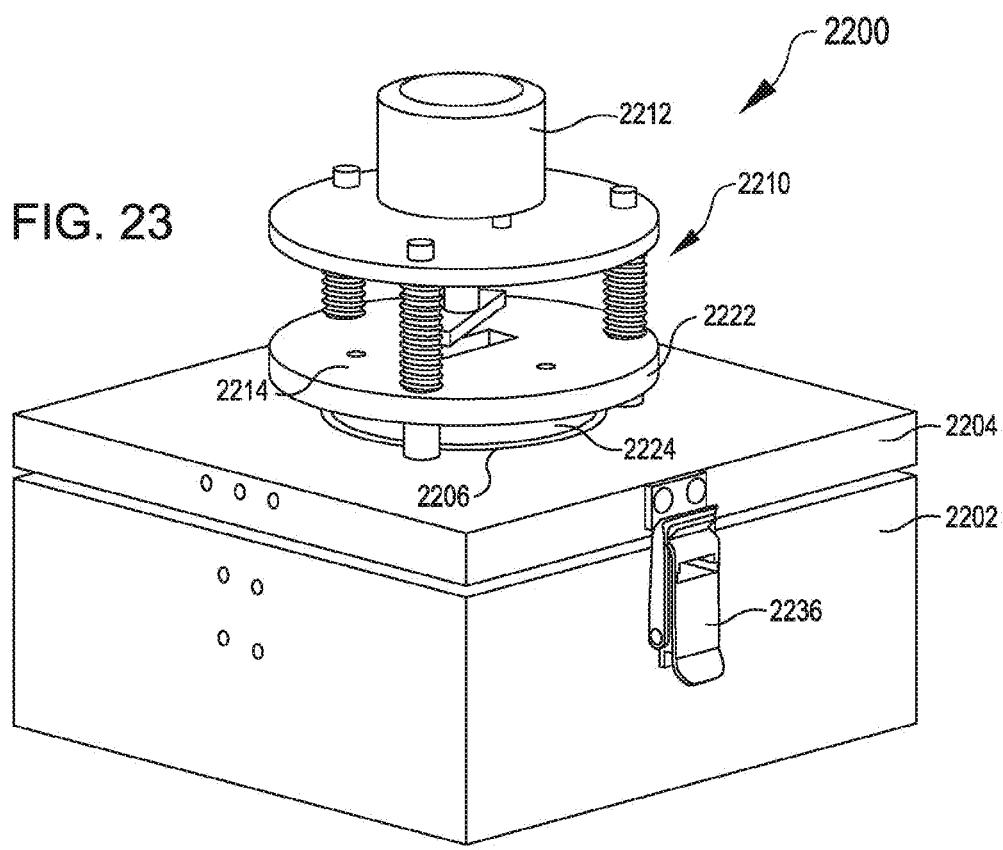

FIGS. 15-17 illustrate a first example of an electromagnetic sealing mechanism 1500. In FIGS. 15-16, a shaft 1502 is connected to a trap door 1504 (or valve) and is routed through (or otherwise placed within range of) an electromagnet 1506 of an electromagnetic actuator. The shaft 1502 may be connected with the trap door 1504 in such a manner that the trap door 1504 and shaft 1502 are constrained to move together as a unit. A compression spring 1508 (or other biasing mechanism) is arranged to exert a force on the shaft 1502 (which may also form part of the electromagnetic actuator) so as to bias the trap door 1504 toward a closed position such as the state shown in FIG. 15 (e.g., the compression spring 1508 can be positioned between the electromagnet 1506 and a base 1510 of the support shaft 1502). The compression spring 1508 may cause the trap door 1504 to move toward and/or remain in a closed position when the electromagnet 1506 is not energized. Hence the system may be considered a "normally-closed" arrangement. Energizing the electromagnet 1506 produces an axial electromagnetic force (EMF) that exceeds the static force of the compression spring, thus moving the support shaft 1502 and forcing the trap door 1504 to open (e.g., move to the position shown in FIG. 17). In the embodiment illustrated in FIGS. 15-17, the electromagnet 1506 may be supplied with power and/or control signals from an electronic control unit (which is not shown in FIG. 15-17, but which may correspond the electronic control unit 34 described with respect to FIG. 1 above or to any other suitable electronics package for providing power and/or control signals). The electronic control unit of the sterilization tray can provide a small electric charge to the electromagnet 1506 from the very beginning of the sterilization cycle (or other relevant point relative to the cycle) and maintain the charge to keep the trap door 1504 in an open state (such as the state shown in FIG. 17) until a desired point of the cycle is reached, e.g., based on time and/or environmental conditions within the autoclave (such as temperature, pressure, humidity, etc.). Once the target point is reached, the electromagnet 1506 can be de-energized, allowing the compression spring 1508 to pull the trap door 1504 closed, thereby sealing the tray (e.g., via contact between the trap door 1504 and a gasket 1512 visible in FIG. 17).

FIGS. 18-21 illustrate another example of an electromagnetic sealing mechanism 1600. Once again, a shaft 1612 is connected to a trap door 1604 (or valve) and is routed through (or otherwise placed within range of) an electromagnet 1606. The electromagnet 1606 may be part of an electromagnetic actuator, which may include the shaft 1612. The shaft 1602 may be connected with the trap door 1604 in such a manner that the trap door 1604 and shaft 1602 are constrained to move together as a unit. In this embodiment, a compression spring 1608 (or other biasing mechanism) is arranged to exert a force on the shaft 1602 so as to bias the trap door 1604 toward an open position such as the state shown in FIG. 18 (e.g., the compression spring 1608 may be positioned between the electromagnet 1606 and the trap door 1604). The compression spring 1608 may cause the trap door 1604 to move toward and/or remain in an open position when the electromagnet 1506 is not energized (e.g., the spring 1608 may bias the shaft 1602 upward to a point at which a base 1610 of the shaft 1602 contacts another surface and constrains further movement of the shaft 1602). Hence the system may be considered a "normally-open" arrangement. Upon energizing the electromagnet 1606, an axial EMF exceeds the static force of the compression spring 1608, thereby forcing the trap door 1604 to close (e.g., move to the position shown in FIGS. 20-21). Although the spring 1608 is shown abutting the electromagnet 1606 in FIG. 21, in some cases, the spring 1608 may abut against a different surface (e.g., the spring 1608 may be positioned outside of a field of effect of the electromagnet, such as in a situation in which the spring 1608 abuts a surface disposed between the electromagnet 1606 and the spring 1608). In this "normally-open" embodiment, the electromagnet 1606 may be de-energized for most of the sterilization cycle, then an electronic control unit (e.g., similar to that described above with respect to FIGS. 15-17) can deliver a small electric charge to the electromagnet 1606 once the desired point of the cycle is reached, e.g., based on time and/or environmental conditions within the autoclave (such as temperature, pressure, humidity, etc.). This charge can work against the force of the compression spring 1608 to pull the trap door 1604 closed and seal the tray. In this arrangement, the electromagnet 1606 may remain energized to keep the trap door 1604 closed, for example, until the environment surrounding the tray is restored to atmospheric pressure. Once the environment outside the tray is restored to atmospheric pressure, the trap door 1604 may remain closed primarily due to a pressure differential existing between the volume inside the tray and the outside world. The pressure differential may be maintained by the hermetic seal. The pressure differential may bias the trap door toward closed and sealed in any configuration disclosed herein. In various embodiments, the hermetic seal is most easily maintained by the trap door being slightly larger than the opening (or portal) provided through the lid of the tray.

As described above, both of the illustrated embodiments of the electro-magnetic sealing mechanisms 1500/1600 can involve latching the trap door 1504/1604 either open or closed for a duration of time. Latching in a particular position can be achieved by providing a small electric charge to the electromagnet 1506/1606 for a duration of time in which the trap door 1504/1604 is to remain latched. Additionally, or alternatively, the trap door assembly 1504/1604 can be magnetically latched in the desired state (e.g., by one or more magnets 1514/1614 arranged on or in the trap door 1504/1604 and/or some other portion of the container to engage the trap door 1504/1604 and/or the support shaft 1502/1602 when the trap door 1504/1604 is in the desired state). This may reduce or eliminate a need to provide a steady charge to the electromagnet 1506/1606. With such configurations, a short pulse of charge would de-latch the trap door from a static or latched state, allowing the trap door 1504/1604 to move to the next state, where it would be latched anew (e.g., by the positioned magnets or the compression spring 1504/1604).

Other variations on the electro-magnetic sealing mechanisms 1500/1600 are also possible. For example, although each of the illustrated electro-magnetic sealing mechanisms 1500/1600 are described above as arranged such that respective shafts 1502/1602 are acted on by respective electromagnets 1506/1606, in some embodiments, the electromagnets 1506/1606 may additionally or alternatively act directly on the trap door 1504/1604 or other structure coupled thereto to push the trap door 1504/1604 in a certain direction under the influence of electromagnetic force produced by the electromagnet. Thus, an electromagnet 1504/1506 may be utilized to push a respective trap door 1504/1506 even if a shaft 1502/1506 is omitted and/or replaced with other structure for guiding movement of the trap door 1504/1506 (e.g., which may include, but is not limited to the mounts 38 illustrated in FIG. 1 etc. and described above). Additionally, although each of the illustrated electro-magnetic sealing mechanisms 1500/1600 and shafts 1502/1602 are shown located at least partially inside a container, in some embodiments any of these elements may additionally or alternatively be located at least partially outside of the container.

Additionally, in some embodiments, an electromagnet 1506/1606 described herein may include a bi-stable electromagnet. Such a bi-stable electromagnet may be capable of exerting a magnetic force of a first magnitude and orientation when not energized and also capable of altering the magnitude and/or orientation of the magnetic force in response to being energized. For example, a permanent magnet may provide a first magnitude and alignment of a magnetic force in the absence of energizing a nearby coil, and energizing the nearby coil may produce additional magnetic fields that will alter an overall magnitude and orientation of magnetic force provided. In some aspects, a bi-stable electromagnet may be capable of exerting different magnitudes and/or orientations of magnetic forces based on receiving different types of energizing. For example, in some cases, an electromagnet may include two coils spaced apart so that a plunger or other movable magnetically couplable structure will be drawn toward whichever of the two coils is energized. In some embodiments, use of a bi-stable electromagnet may permit a compression spring 1508/1608 to be omitted (e.g., an electromagnet that is bi-stable may provide the opening, closing, and/or maintaining force that might otherwise be provided by the compression spring 1508/1608). As an example, referring to FIGS. 19 and 21, an electromagnet 1606 that is bi-stable may be capable of exerting a sufficient electromagnetic force in a de-energized state to maintain the trap door 1604 in the open state shown in FIG. 19, exerting a sufficient electromagnetic force in a first energized state to push the trap door 1604 to the closed state shown in FIG. 21, exerting a sufficient electromagnetic force in a de-energized state to maintain the trap door 1604 in the closed state shown in FIG. 21, and exerting a sufficient electromagnetic force in a second energized state to push the trap door 1604 to the open state shown in FIG. 19. Such functionality may permit the electromagnet 1606 that is bi-stable to function to push the trap door 1604 in suitable directions to open, close, and/or latch the trap door 1604 as desired at different points in the sterilization cycle, for example in response to any suitable combination of environmental factors.

Solenoid Keyhole Sealing Mechanisms

FIG. 22-32 illustrate another embodiment of a self-sealing sterilization tray 2200. The tray includes a base portion 2202 (that receives items to be sterilized) and a lid 2204 that sealingly interfaces with the base 2202. The lid 2204 has a vent 2206 providing fluid communication between the internal volume 2208 (e.g., defined by the base 2202 and cover 2204 and illustrated in FIG. 22 as visible through a cutout 2218 that is included merely for illustrative purposes) and the external volume 2220 (e.g., a volume or environment within a sterilization chamber). The apparatus 2200 has a sealing assembly 2210 that uses actuation of a rotary solenoid 2212 to move a trap door 2214 from an open position (e.g., FIG. 22, in which fluid communication through the vent 2206 is unobstructed) to a closed position (e.g., FIG. 23, in which the trap door 2214 engages a gasket 2216 about the vent 2206 to cut off fluid communication through the vent 2206 and hermetically seal the internal volume 2208).

Figure 24:
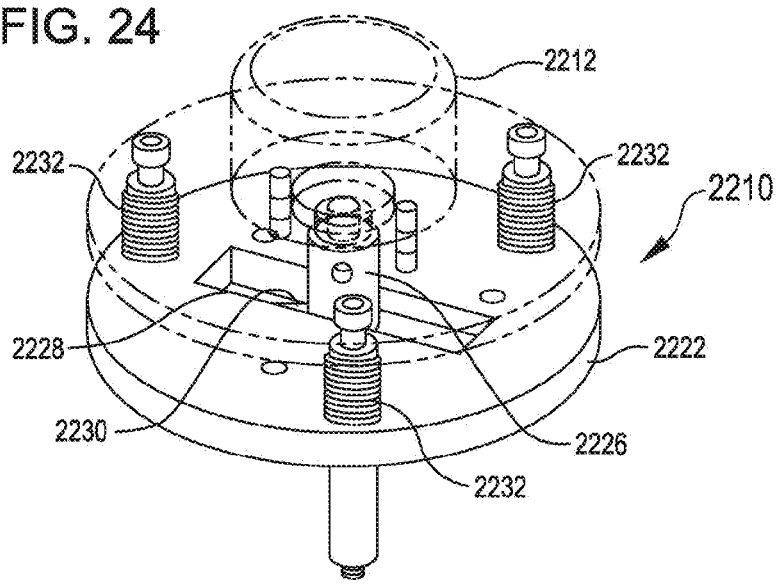
Figure 25:
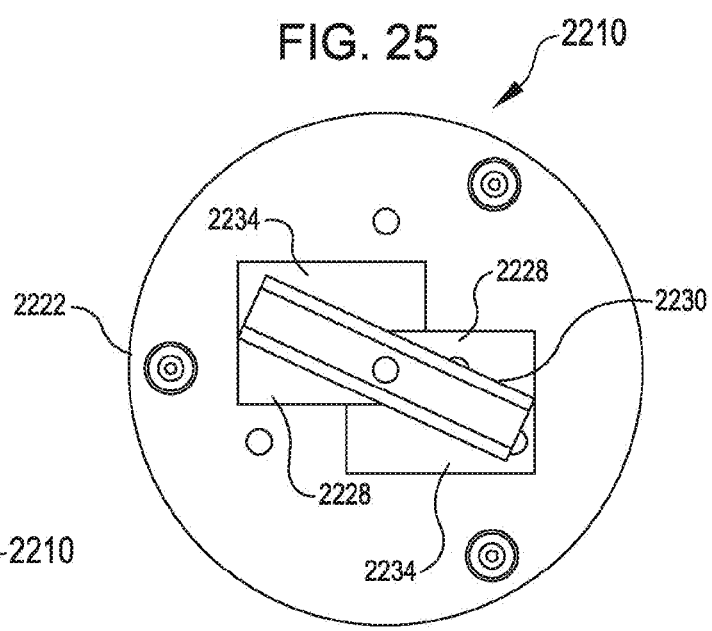
Figure 26:
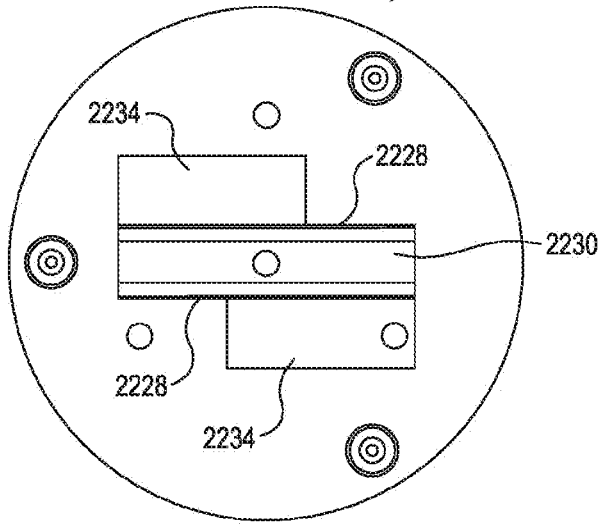
Figure 27:
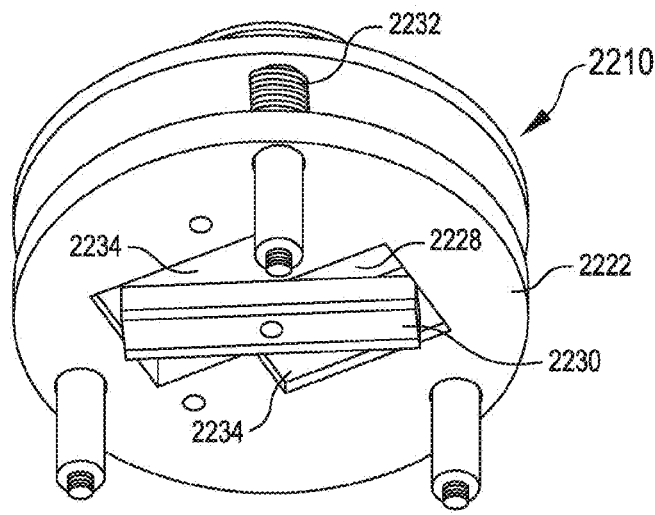
Figure 28:
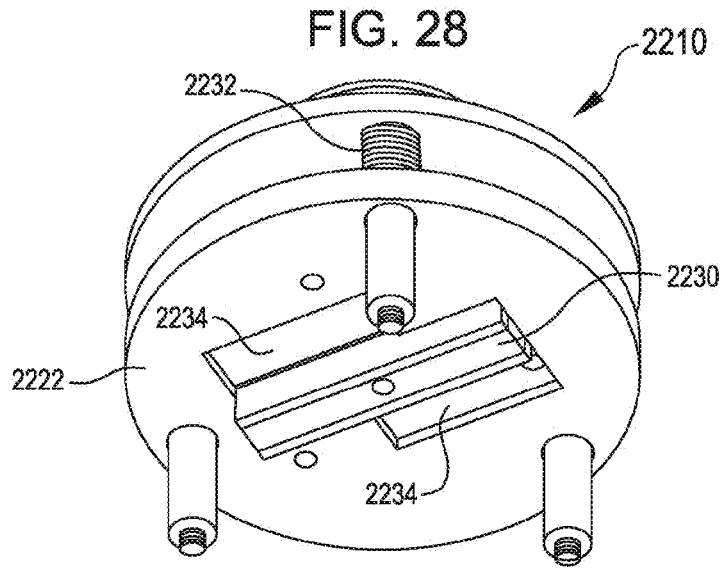
Figure 29:
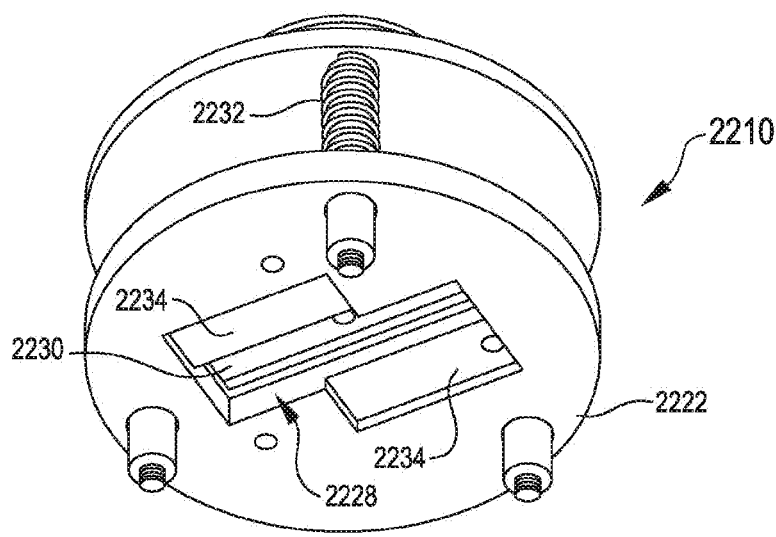
Figure 30:
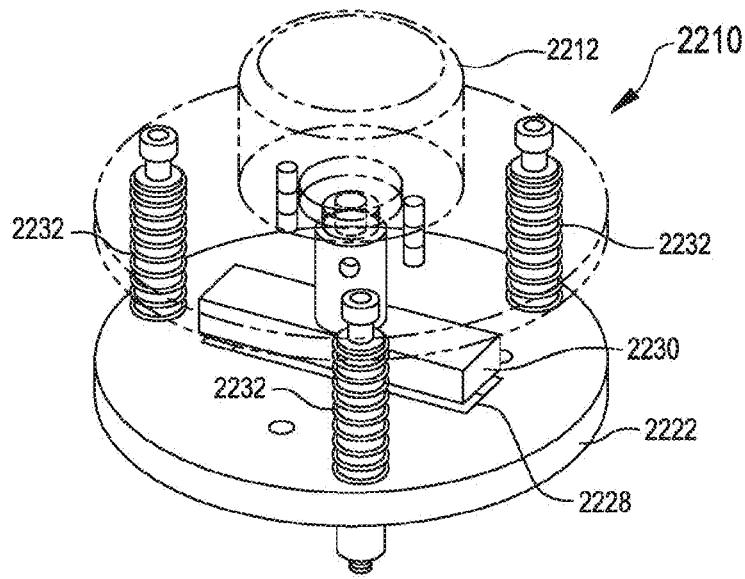

The trap door 2214 shown in the drawings has a top plate 2222 and a bottom plate 2224. The sealing assembly 2210 is shown in FIG. 24 with the bottom plate 2224 of the trap door 2214 removed to aid visibility. As seen in FIG. 24, when the trap door 2214 is in the open position, a shaft 2226 extends from the rotary solenoid 2212 through a slot 2228 in the top plate 2222. The shaft 2226 is attached (e.g., at an end) to a key latch 2230 (e.g., more easily seen in FIG. 25). In a primed position shown in FIG. 24, the key latch 2230 is positioned across the slot 2228 so as to hold the top plate 2222 up against a downward force exerted by springs 2232 (or other biasing mechanisms) on the top plate 2222. For example, as illustrated in FIG. 25, the key latch 2230 can extend into grooves 2234 on either side of the slot 2228 on the bottom of the top plate 2222. Turning of the rotary solenoid 2212 can rotate the key latch 2230 (e.g., out of the grooves 2234, such as illustrated in FIG. 26) so that the key latch 2230 aligns with the slot 2228. This alignment allows the slot 2228 to move past the sides of the key latch 2230 and allows the top plate 2222 to move downward under the force of the springs 2232 past the key latch 2230 (e.g., as illustrated by FIGS. 27-29, culminating in the arrangement shown in FIG. 30). In some embodiments, the key latch 2230 may be positioned completely above or out of the slot 2228 when the top plate 2222 has moved into the closed position (e.g., as shown in FIG. 30), or at any other position relative to the height of the slot 2228 (e.g., including at least partially in the slot 2228 as in FIG. 31).

Figure 31:
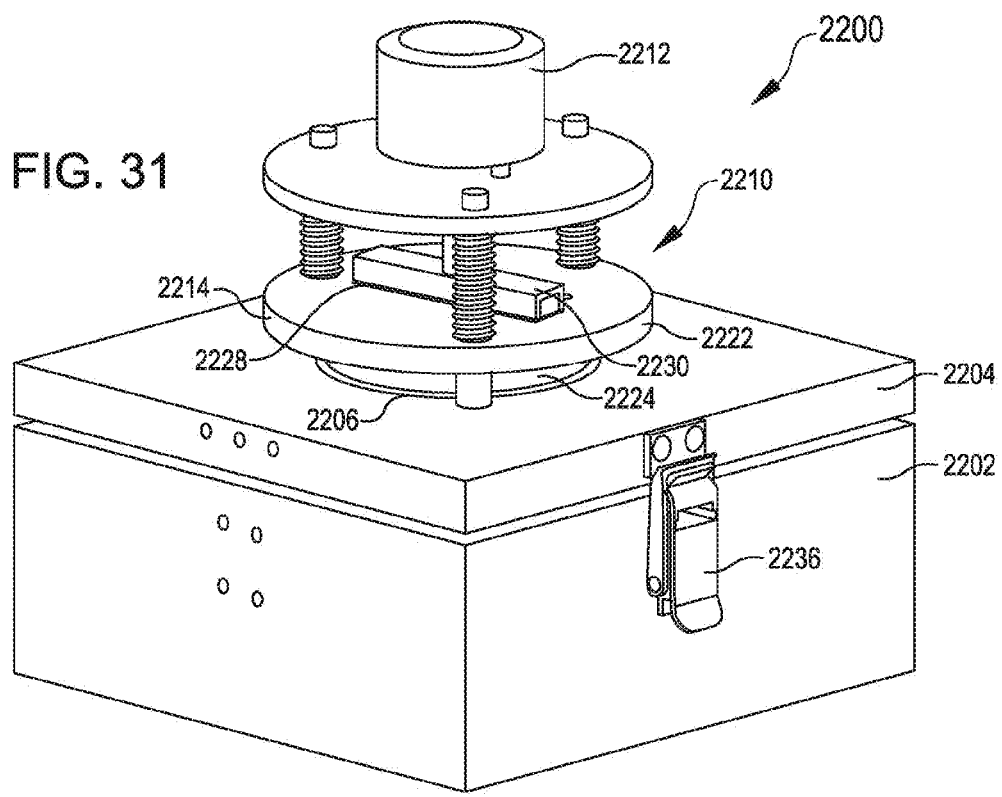
Figure 32:
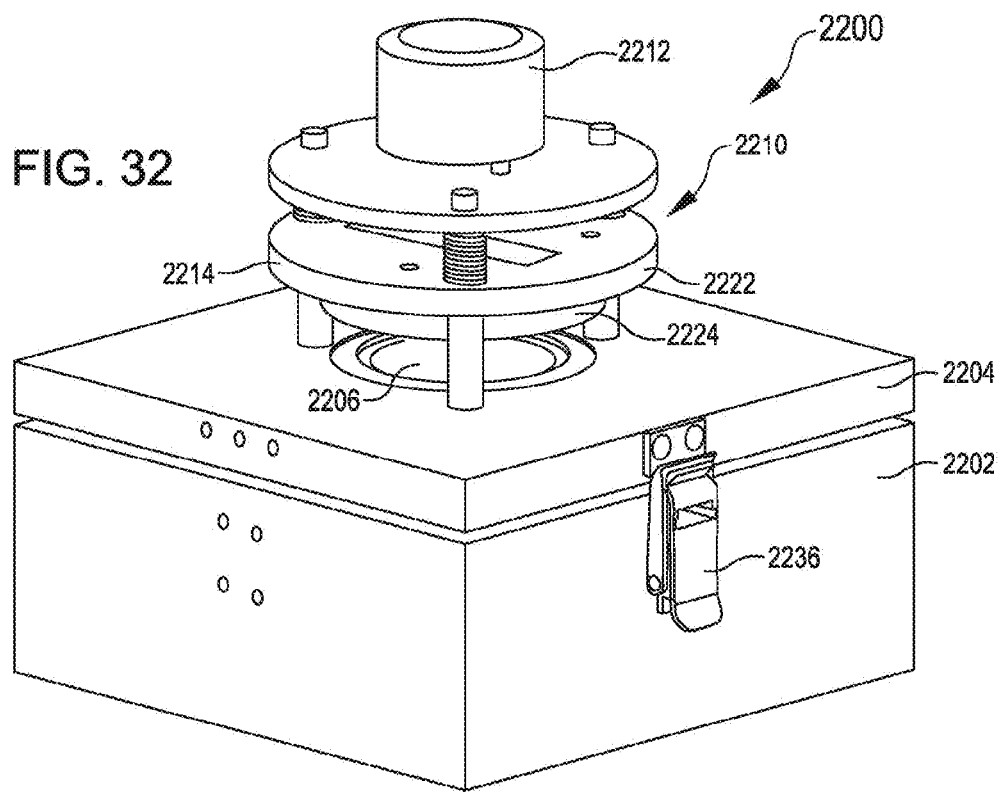

A latch 2236 or other securing mechanism 2236 holding the lid 2204 and base 2202 together may be released to gain access to the sterilized items for use. Additionally, in some embodiments, the sealing assembly 2210 can be reused by reconfiguring the assembly from the deployed or sealed position to the primed position (e.g., from the position shown in FIG. 31 to the position shown in FIG. 32). In various embodiments, to reset the sealing assembly 2210 in preparation for a subsequent use, the trap door 2214 can be reset by raising the trap door 2214 and turning the key latch 2230 back into the primed position. For example, the trap door 2214 may be raised by manually applying a force to lift the trap door 2214 above the level of the top of the key latch 2230 (e.g., as depicted in FIG. 31). Lifting the trap door 2214 above the top level of the key latch 2230 may allow a torsional spring (not shown) within the rotary solenoid 2212 to rotate the key latch 2230 back into the grooves 2234 on the bottom of the top plate 2222 (e.g., from the arrangement illustrated in FIG. 26 to the arrangement illustrated in FIG. 25), which may re-secure the trap door 2214 in a primed position. In some embodiments, the rotary solenoid 2212 can be operated to turn the key latch 2230 in lieu of or in addition to the use of a torsional spring. Moreover, in some embodiments, manual lifting of the trap door 2214 by replaced and/or supplemented by a different manner of lifting the trap door 2214, such as by using an electromagnet similar to that described with respect to the Electro-Magnetic Sealing Mechanisms described above with reference to FIGS. 18-21 and/or by implementing some other automated lifting technique.

In various embodiments, the bottom plate 2224 may provide a solid or non-perforated surface that can seal against the vent 2206, while the top plate 2222 may provide suitable features for receiving elements that facilitate actuation of the trap door 2214. In some aspects, the sealing assembly 2210 may have a different construction than that just described. For example, the top plate 2222 and the bottom plate 2224 may be a single piece (e.g., with internal voids corresponding to the features of the top plate 2222 for receiving the key latch 2230 etc.) or any other suitable construction of single or multiple pieces. Moreover, although the illustrated depictions include specific shapes such as a rectangular key latch 2230 or a round trap door 2214, embodiments are not so limited and may incorporate any suitable shape for these and/or other elements.

Power Generation

Most materials possess the ability to generate an electric potential between two different points within the material when a temperature gradient exists across the material. The phenomenon is typically referred to as the thermoelectric effect of the material and can be harnessed in such way to allow for the generation of electricity.

In most metals, the thermoelectric effect is relatively small for practical purposes but several materials may be able to generate a notable level of electricity during a sterilization cycle to provide primary and/or supplementary power to the electronic control system or rechargeable batteries within a sterilization tray. Examples of such materials may include bismuth telluride, tetrahedrite, bismuth chalcogenides, inorganic clathrates, magnesium compounds, tin selenide, skutterudite, silicides.

Typically, the primary objective of an autoclave is to sterilize the contents within the chamber with heat. During a typical sterilization cycle, temperature within the autoclave will typically rise from room temperature (~75° F.) to approximately 260° F., then cycle between 260° F. and approximately 160° F. for three or four pulses as part of the pre-evacuation of the sterilization cycle with the temperature of the autoclave being held at these extremes for a short duration of time (e.g., on the order of several seconds) before climbing and holding for a longer duration of time (e.g., on the order of several minutes) at a sterilization temperature of approximately 270° F. Upon completion of sterilization, the temperature within the chamber drops to below 200° F. and remains elevated above room temperature until the autoclave is opened and the contents are allowed to passively cool. Up until the point at which the autoclave is opened and the contents are allowed to cool, the temperature changes within the autoclave occur relatively fast with the temperature changing over several decades in either direction within a matter of approximately 30 seconds.

Figure 33:
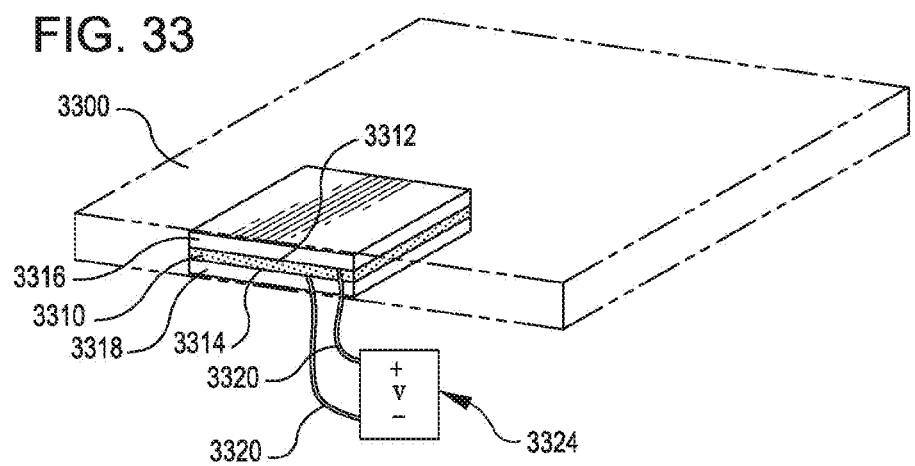
FIG. 33 illustrates an example of a thermoelectric generator that can be used with various embodiments herein.

If one or more thermoelectric materials or generators 3310 are embedded within an external surface 3300 such as the lid, wall, or floor of a tray (e.g., as illustrated in FIG. 33), or if the entire tray base and/or lid were constructed in such a way that the entire surface 3300 was a generator, the rapid temperature changes within the autoclave may provide the necessary thermal energy to the thermoelectric material to generate electrical energy.

For example, the thermoelectric generator 3310 can use a temperature gradient between two faces 3312 and 3314 to generate an electric potential. The generator 3310 can be sandwiched between a first layer 3316 and a second layer 3318 respectively corresponding to two materials with differing specific thermal conductivity characteristics. Such a construction, in combination with the rapid changes in temperature in an autoclave, may provide a mechanism for generating a temperature gradient across the faces 3312 and 3314 of the generator 3310. Specifically, comparing between the first layer 3316 and the second layer 3318, the first layer 3316 (e.g., exposed to the exterior of the surface 3300) can include materials having a higher thermal conductivity that will cause the material in the first layer 3316 to change temperature relatively rapidly, and the second layer 3318 (e.g., further from the exterior of the surface 3300) can include material having a lower thermal conductivity that will cause the material in the second layer 3318 to change temperature relatively slowly. As the temperature changes within the autoclave, the face 3312 of the generator 3310 along the first layer 3316 of more thermally conductive material may be expected to closely follow the temperature of the autoclave; however, the face 3314 of the generator 3310 along the second layer 3318 of less thermally conductive material may be expected to lag behind the temperature within the autoclave. This may be expected to create a temperature gradient between the two faces 3312 and 3314 and generate an electric potential 3324 e.g., which may be harnessed using suitable electrical leads 3320, such as to power the system and/or to recharge a battery pack.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method comprising reconfiguring a trap door of a container to an open configuration prior to or during a target portion of a sterilization cycle for one or more surgical implements by providing instructions from a control unit to cause an electromagnetic actuator housed in the container or housed directly on the container to push the trap door toward the open configuration, the trap door reconfigurable between a closed configuration in which the trap door and the container at least partially define an internal volume of the container that is sealed and the open configuration in which the trap door is displaced from the container to form a fluid passage between the internal volume and an external volume within a sterilization chamber and external to the container.

2. The method of claim 1, wherein the reconfiguring the trap door to the open configuration comprises energizing the electromagnetic actuator to push the trap door toward the open configuration with an amount of force sufficient to overcome a biasing force that is provided by a biasing mechanism and that biases the trap door toward the closed configuration.

3. The method of claim 1, further comprising reconfiguring the trap door to the closed configuration at an end of the target portion of the sterilization cycle.

4. The method of claim 3, wherein the reconfiguring the trap door to the closed configuration comprises controlling the electromagnetic actuator to pull the trap door toward the closed configuration.

5. The method of claim 1, wherein the reconfiguring the trap door to the open configuration prior to or during the target portion of the sterilization cycle comprises reconfiguring the trap door to the open configuration prior to the target portion of the sterilization cycle.

6. The method of claim 1, wherein the reconfiguring the trap door to the open configuration prior to or during the target portion of the sterilization cycle comprises reconfiguring the trap door to the open configuration during the target portion of the sterilization cycle.

7. A method comprising reconfiguring a trap door of a container to an open configuration prior to or during a target portion of a sterilization cycle for one or more surgical implements by providing instructions from a control unit to cause an electromagnetic actuator housed in the container or housed directly on the container to pull the trap door toward the open configuration, the trap door reconfigurable between a closed configuration in which the trap door and the container at least partially define an internal volume of the container that is sealed and the open configuration in which the trap door is displaced from the container to form a fluid passage between the internal volume and an external volume within a sterilization chamber and external to the container.

8. The method of claim 7, wherein the reconfiguring the trap door to the open configuration comprises energizing the electromagnetic actuator to pull the trap door toward the open configuration with an amount of force sufficient to overcome a biasing force that is provided by a biasing mechanism and that biases the trap door toward the closed configuration.

9. The method of claim 7, further comprising reconfiguring the trap door to the closed configuration at an end of the target portion of the sterilization cycle.

10. The method of claim 9, wherein the reconfiguring the trap door to the closed configuration comprises controlling the electromagnetic actuator to push the trap door toward the closed configuration.

11. The method of claim 7, wherein the reconfiguring the trap door to the open configuration prior to or during the target portion of the sterilization cycle comprises reconfiguring the trap door to the open configuration prior to the target portion of the sterilization cycle.

12. The method of claim 7, wherein the reconfiguring the trap door to the open configuration prior to or during the target portion of the sterilization cycle comprises reconfiguring the trap door to the open configuration during the target portion of the sterilization cycle.

13. A method comprising reconfiguring a trap door of a container to an open configuration prior to or during a target portion of a sterilization cycle for one or more surgical implements by providing instructions from a control unit housed in the container or housed directly on the container to cause an electromagnetic actuator to move the trap door toward the open configuration, the trap door reconfigurable between a closed configuration in which the trap door and the container at least partially define an internal volume of the container that is sealed and the open configuration in which the trap door is displaced from the container to form a fluid passage between the internal volume and an external volume within a sterilization chamber and external to the container.

14. The method of claim 13, wherein the reconfiguring the trap door to the open configuration comprises energizing the electromagnetic actuator to move the trap door toward the open configuration with an amount of force sufficient to overcome a biasing force that is provided by a biasing mechanism and that biases the trap door toward the closed configuration.

15. The method of claim 13, further comprising reconfiguring the trap door to the closed configuration at an end of the target portion of the sterilization cycle.

16. The method of claim 15, wherein the reconfiguring the trap door to the closed configuration comprises controlling the electromagnetic actuator to move the trap door toward the closed configuration.

17. The method of claim 13, wherein the reconfiguring the trap door to the open configuration prior to or during the target portion of the sterilization cycle comprises reconfiguring the trap door to the open configuration prior to the target portion of the sterilization cycle.

18. The method of claim 13, wherein the reconfiguring the trap door to the open configuration prior to or during the target portion of the sterilization cycle comprises reconfiguring the trap door to the open configuration during the target portion of the sterilization cycle.

19. The method of claim 13, wherein the instructions from the control unit to cause the electromagnetic actuator to move the trap door toward the open configuration include instructions from the control unit to cause the electromagnetic actuator to push the trap door toward the open configuration.

20. The method of claim 13, wherein the instructions from the control unit to cause the electromagnetic actuator to move the trap door toward the open configuration include instructions from the control unit to cause the electromagnetic actuator to pull the trap door toward the open configuration.

\* \* \* \* \*